(12) United States Patent
Takamatsu et al.

(10) Patent No.: US 8,956,868 B2
(45) Date of Patent: Feb. 17, 2015

(54) INDUCED PLURIPOTENT STEM CELLS PRODUCED WITH A CONNEXIN INHIBITOR AND A TGF-β SIGNALING INHIBITOR

(75) Inventors: Tetsuro Takamatsu, Kyoto (JP); Ping Dai, Kyoto (JP)

(73) Assignee: LSIP, LLC, Tokyo (JP)

( * ) Notice: Subject to any disclaimer, the term of this patent is extended or adjusted under 35 U.S.C. 154(b) by 283 days.

(21) Appl. No.: 13/337,767

(22) Filed: Dec. 27, 2011

(65) Prior Publication Data

US 2012/0214234 A1    Aug. 23, 2012

Related U.S. Application Data

(60) Provisional application No. 61/427,354, filed on Dec. 27, 2010.

(51) Int. Cl.
| | |
|---|---|
| *C12N 5/02* | (2006.01) |
| *C12N 5/074* | (2010.01) |
| *C12N 5/0735* | (2010.01) |
| *C12N 5/071* | (2010.01) |

(52) U.S. Cl.
CPC ........ *C12N 5/0696* (2013.01); *C12N 2501/605* (2013.01); *C12N 2501/603* (2013.01); *C12N 2501/10* (2013.01); *C12N 2506/45* (2013.01); *C12N 2501/604* (2013.01); *C12N 2501/999* (2013.01); *C12N 2501/608* (2013.01); *C12N 5/0606* (2013.01); *C12N 2501/606* (2013.01); *C12N 2501/60* (2013.01); *C12N 2501/602* (2013.01); *C12N 5/0678* (2013.01); *C12N 2506/1307* (2013.01); *C12N 2500/99* (2013.01); *C12N 2501/19* (2013.01); *C12N 2310/14* (2013.01); *C12N 2501/15* (2013.01); *C12N 2501/998* (2013.01); *C12N 2506/1315* (2013.01)
USPC ........... 435/377; 435/373; 435/384; 435/395; 435/402

(58) Field of Classification Search
CPC ....... A61N 1/3605; A61N 1/362; A61N 1/37; A61N 1/3956; C12N 5/0696; C12N 2501/15; C12N 2501/603; C12N 2501/604; C12N 2501/999; C12N 2501/602; C12N 2501/606; C12N 2501/10; C12N 5/0678; C12N 2501/60; C12N 2501/605; C12N 2501/608; C12N 2506/1307
See application file for complete search history.

(56) References Cited

PUBLICATIONS

Chadjichristos et al. Targeting Connexin 43 Prevents Platelet-Derived Growth Factor-BB-Induced Phenotypic Change in Porcine Coronary Artery Smooth Muscle Cells. Circulation Res., 2008, vol. 102, pp. 653-660.*
Wilson et al. MicroRNA Profiling of Human-Induced Pluripotent Stem Cells. Stem Cells and Develop., 2009, vol. 18, pp. 1-24.*
Anderson et al. MIR-206 regulates connexin43 expression during skeletal muscle development. Nucleic Acids Research, 2006, vol. 34, No. 20 5863-5871.*
Strelchenko et al. Embryonic Stem Cells From Morula. Methods in Enzym., 2006, vol. 418, pp. 93-108.*
Stojovic et al. Derivation, growth and applications of human embryonic stem cells. Reproduction, 2004, vol. 128, pp. 259-267.*
Asazuma-Nakamura et al.. *Experimental Cell Research*, 315(7): 1190-1199 (2009).
Ichida et al., *Cell Stem Cell*, 5(5): 491-503 (2009).
Lin et al., *Nature Methods*, 6(11): 805-808 (2009).
Maherall et al., *Current Biology*, 19(20): 1718-1723 (2009).
Okita et al., *Nature*, 448: 313-317 (2009).
Pasha et al., *PLoS One*, 6(8): e23667 (2011).
Rhett et al., *Trends Biotechnology*, 26(4): 173-180 (2008).
Takahashi et al., *Cell*, 126: 663-676 (2006).
T. Aasen, et al., "Efficient and Rapid Generation of Induced Pluripotent Stem Cells from Human Keratinocytes," Nature Biotechnology, vol. 26, No. 11, Nov. 2008, pp. 1276-1284.

* cited by examiner

*Primary Examiner* — Deborah Crouch
(74) *Attorney, Agent, or Firm* — Hogan Lovells US LLP

(57) ABSTRACT

The present invention provides a method for producing iPS cells, comprising reacting cells with at least one connexin inhibitor and at least one TGFβ signaling inhibitor; iPS cells comprising at least one connexin inhibitor; an iPS cell inducer comprising at least one inhibitor selected from the group consisting of connexin inhibitors and TGFβ signaling inhibitors; a medium for inducing iPS cells, comprising at least one inhibitor selected from the group consisting of connexin inhibitors and TGFβ signaling inhibitors; and a kit for inducing iPS cells, comprising at least one inhibitor selected from the group consisting of connexin inhibitors and TGFβ signaling inhibitors.

11 Claims, 2 Drawing Sheets

SEQUENCE LISTING

```
<160> NUMBER OF SEQ ID NOS: 126

<210> SEQ ID NO 1
<211> LENGTH: 20
<212> TYPE: DNA
<213> ORGANISM: Artificial Sequence
<220> FEATURE:
<223> OTHER INFORMATION: Synthetic Cx43 siRNA sense
<220> FEATURE:
<223> OTHER INFORMATION: This is a combined DNA/RNA sequence

<400> SEQUENCE: 1
caauucuucu ugccgcaatt                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic Cx43 siRNA antisense
<220> FEATURE:
<223> OTHER INFORMATION: This is a combined DNA/RNA sequence

<400> SEQUENCE: 2
uugcggcaag aagaauugtt                                              20

<210> SEQ ID NO 3
<211> LENGTH: 30
<212> TYPE: DNA
<213> ORGANISM: Artificial Sequence
<220> FEATURE:
<223> OTHER INFORMATION: Synthetic Cx43 antisense polynucleotide

<400> SEQUENCE: 3
gtaattgcgg caagaagaat tgtttctgtc                                   30

<210> SEQ ID NO 4
<211> LENGTH: 30
<212> TYPE: DNA
<213> ORGANISM: Artificial Sequence
<220> FEATURE:
```

<223> OTHER INFORMATION: Synthetic Cx43 antisense polynucleotide

<400> SEQUENCE: 4
gtaattgcgg caggaggaat tgtttctgtc                                    30

<210> SEQ ID NO 5
<211> LENGTH: 30
<212> TYPE: DNA
<213> ORGANISM: Artificial Sequence
<220> FEATURE:
<223> OTHER INFORMATION: Synthetic Cx43 antisense polynucleotide

<400> SEQUENCE: 5
ggcaagagac accaaagaca ctaccagcat                                    30

<210> SEQ ID NO 6
<211> LENGTH: 27
<212> TYPE: DNA
<213> ORGANISM: Artificial Sequence
<220> FEATURE:
<223> OTHER INFORMATION: Synthetic Cx26 antisense polynucleotide

<400> SEQUENCE: 6
tcctgagcaa tacctaacga acaaata                                       27

<210> SEQ ID NO 7
<211> LENGTH: 20
<212> TYPE: DNA
<213> ORGANISM: Artificial Sequence
<220> FEATURE:
<223> OTHER INFORMATION: Synthetic Cx37 antisense polynucleotide

<400> SEQUENCE: 7
catctccttg gtgctcaacc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Cx37 antisense polynucleotide

<400> SEQUENCE: 8
ctgaagtcga cttggcttgg                                               20

<210> SEQ ID NO 9
<211> LENGTH: 21
<212> TYPE: DNA
<213> ORGANISM: Artificial Sequence
<220> FEATURE:
<223> OTHER INFORMATION: Synthetic Cx30 antisense polynucleotide

<400> SEQUENCE: 9
ctcagatagt ggccagaatg c                                             21

<210> SEQ ID NO 10
<211> LENGTH: 20
<212> TYPE: DNA
<213> ORGANISM: Artificial Sequence
<220> FEATURE:
<223> OTHER INFORMATION: Synthetic Cx30 antisense polynucleotide

<400> SEQUENCE: 10
ttgtccaggt gactccaagg                                               20

```
<210> SEQ ID NO 11
<211> LENGTH: 25
<212> TYPE: DNA
<213> ORGANISM: Artificial Sequence
<220> FEATURE:
<223> OTHER INFORMATION: Synthetic Cx31.1 antisense polynucleotide

<400> SEQUENCE: 11
cgtccgagcc cagaaagatg aggtc                                              25

<210> SEQ ID NO 12
<211> LENGTH: 19
<212> TYPE: DNA
<213> ORGANISM: Artificial Sequence
<220> FEATURE:
<223> OTHER INFORMATION: Synthetic Cx31.1 antisense polynucleotide

<400> SEQUENCE: 12
agaggcgcac gtgagacac                                                     19

<210> SEQ ID NO 13
<211> LENGTH: 19
<212> TYPE: DNA
<213> ORGANISM: Artificial Sequence
<220> FEATURE:
<223> OTHER INFORMATION: Synthetic Cx31.1 antisense polynucleotide

<400> SEQUENCE: 13
tgaagacaat gaagatgtt                                                     19

<210> SEQ ID NO 14
<211> LENGTH: 25
<212> TYPE: DNA
<213> ORGANISM: Artificial Sequence
<220> FEATURE:
<223> OTHER INFORMATION: Synthetic Cx32 antisense polynucleotide

<400> SEQUENCE: 14
tttcttttct atgtgctgtt ggtga                                              25

<210> SEQ ID NO 15
<211> LENGTH: 11
<212> TYPE: PRT
<213> ORGANISM: Homo sapiens

<400> SEQUENCE: 15

Phe Glu Val Ala Phe Leu Leu Ile Gln Trp Ile
1               5                   10

<210> SEQ ID NO 16
<211> LENGTH: 11
<212> TYPE: PRT
<213> ORGANISM: Homo sapiens

<400> SEQUENCE: 16

Leu Leu Ile Gln Trp Tyr Ile Gly Phe Ser Leu
1               5                   10

<210> SEQ ID NO 17
<211> LENGTH: 16
<212> TYPE: PRT
<213> ORGANISM: Homo sapiens

<400> SEQUENCE: 17

Ser Leu Ser Ala Val Tyr Thr Cys Lys Arg Asp Pro Cys Pro His Gln
1               5                   10                  15
```

```
<210> SEQ ID NO 18
<211> LENGTH: 12
<212> TYPE: PRT
<213> ORGANISM: Homo sapiens

<400> SEQUENCE: 18

Val Asp Cys Phe Leu Ser Arg Pro Thr Glu Lys Thr
1               5                   10

<210> SEQ ID NO 19
<211> LENGTH: 11
<212> TYPE: PRT
<213> ORGANISM: Homo sapiens

<400> SEQUENCE: 19

Ser Arg Pro Thr Glu Lys Thr Ile Phe Ile Ile
1               5                   10

<210> SEQ ID NO 20
<211> LENGTH: 13
<212> TYPE: PRT
<213> ORGANISM: Homo sapiens

<400> SEQUENCE: 20

Leu Gly Thr Ala Val Glu Ser Ala Trp Gly Asp Glu Gln
1               5                   10

<210> SEQ ID NO 21
<211> LENGTH: 12
<212> TYPE: PRT
<213> ORGANISM: Homo sapiens

<400> SEQUENCE: 21

Gln Ser Ala Phe Arg Cys Asn Thr Gln Gln Pro Gly
1               5                   10

<210> SEQ ID NO 22
<211> LENGTH: 12
<212> TYPE: PRT
<213> ORGANISM: Homo sapiens

<400> SEQUENCE: 22

Gln Gln Pro Gly Cys Glu Asn Val Cys Tyr Asp Lys
1               5                   10

<210> SEQ ID NO 23
<211> LENGTH: 13
<212> TYPE: PRT
<213> ORGANISM: Homo sapiens

<400> SEQUENCE: 23

Val Cys Tyr Asp Lys Ser Phe Pro Ile Ser His Val Arg
1               5                   10

<210> SEQ ID NO 24
<211> LENGTH: 12
<212> TYPE: PRT
<213> ORGANISM: Homo sapiens

<400> SEQUENCE: 24

Glu Ser Val Trp Gly Asp Glu Lys Ser Ser Phe Ile
1               5                   10
```

```
<210> SEQ ID NO 25
<211> LENGTH: 12
<212> TYPE: PRT
<213> ORGANISM: Homo sapiens

<400> SEQUENCE: 25

Ile Cys Asn Thr Leu Gln Pro Gly Cys Asn Ser Val
1               5                   10

<210> SEQ ID NO 26
<211> LENGTH: 12
<212> TYPE: PRT
<213> ORGANISM: Homo sapiens

<400> SEQUENCE: 26

Ser Val Cys Tyr Asp His Phe Phe Pro Ile Ser His
1               5                   10

<210> SEQ ID NO 27
<211> LENGTH: 25
<212> TYPE: PRT
<213> ORGANISM: Homo sapiens

<400> SEQUENCE: 27

Arg Leu Val Lys Cys Glu Ala Phe Pro Cys Pro Asn Thr Val Asp Cys
1               5                   10                  15

Phe Val Ser Arg Pro Thr Glu Lys Thr
            20                  25

<210> SEQ ID NO 28
<211> LENGTH: 12
<212> TYPE: PRT
<213> ORGANISM: Homo sapiens

<400> SEQUENCE: 28

Val Lys Cys Glu Ala Phe Pro Cys Pro Asn Thr Val
1               5                   10

<210> SEQ ID NO 29
<211> LENGTH: 12
<212> TYPE: PRT
<213> ORGANISM: Homo sapiens

<400> SEQUENCE: 29

Val Asp Cys Phe Val Ser Arg Pro Thr Glu Lys Thr
1               5                   10

<210> SEQ ID NO 30
<211> LENGTH: 13
<212> TYPE: PRT
<213> ORGANISM: Homo sapiens

<400> SEQUENCE: 30

Val Cys Tyr Asp His Phe Phe Pro Ile Ser His Val Arg
1               5                   10

<210> SEQ ID NO 31
<211> LENGTH: 18
<212> TYPE: PRT
<213> ORGANISM: Homo sapiens

<400> SEQUENCE: 31

Val Trp Gly Asp Glu Lys Ser Ser Phe Ile Cys Asn Thr Leu Gln Pro
1               5                   10                  15
```

Gly Tyr

<210> SEQ ID NO 32
<211> LENGTH: 15
<212> TYPE: PRT
<213> ORGANISM: Homo sapiens

<400> SEQUENCE: 32

Asp Glu Lys Ser Ser Phe Ile Cys Asn Thr Leu Gln Pro Gly Tyr
1               5                   10                  15

<210> SEQ ID NO 33
<211> LENGTH: 11
<212> TYPE: PRT
<213> ORGANISM: Homo sapiens

<400> SEQUENCE: 33

Ser Arg Pro Thr Glu Lys Thr Val Phe Thr Val
1               5                   10

<210> SEQ ID NO 34
<211> LENGTH: 7
<212> TYPE: PRT
<213> ORGANISM: Homo sapiens

<400> SEQUENCE: 34

Ser Arg Pro Thr Glu Lys Thr
1               5

<210> SEQ ID NO 35
<211> LENGTH: 12
<212> TYPE: PRT
<213> ORGANISM: Homo sapiens

<400> SEQUENCE: 35

Ile Cys Asn Thr Leu Gln Pro Gly Cys Asn Ser Val
1               5                   10

<210> SEQ ID NO 36
<211> LENGTH: 16
<212> TYPE: PRT
<213> ORGANISM: Homo sapiens

<400> SEQUENCE: 36

Phe Leu Asp Thr Leu His Val Cys Arg Arg Ser Pro Cys Pro His Pro
1               5                   10                  15

<210> SEQ ID NO 37
<211> LENGTH: 18
<212> TYPE: PRT
<213> ORGANISM: Homo sapiens

<400> SEQUENCE: 37

Lys Arg Asp Pro Cys His Gln Val Asp Cys Phe Leu Ser Arg Pro Thr
1               5                   10                  15

Glu Lys

<210> SEQ ID NO 38
<211> LENGTH: 35
<212> TYPE: PRT
<213> ORGANISM: Homo sapiens

<400> SEQUENCE: 38

Lys Glu Val Trp Gly Asp Glu Gln Ala Asp Phe Val Cys Asn Thr Leu

```
   1               5                  10                  15
Gln Pro Gly Cys Lys Asn Val Cys Tyr Asp His Tyr Phe Pro Ile Ser
                20                  25                  30
His Ile Arg
        35
```

<210> SEQ ID NO 39
<211> LENGTH: 35
<212> TYPE: PRT
<213> ORGANISM: Homo sapiens

<400> SEQUENCE: 39

```
Gln Glu Val Trp Gly Asp Glu Gln Glu Asp Phe Val Cys Asn Thr Leu
1               5                  10                  15
Gln Pro Gly Cys Lys Asn Val Cys Tyr Asp His Phe Phe Pro Val Ser
                20                  25                  30
His Ile Arg
        35
```

<210> SEQ ID NO 40
<211> LENGTH: 35
<212> TYPE: PRT
<213> ORGANISM: Homo sapiens

<400> SEQUENCE: 40

```
Glu Glu Val Trp Asp Asp Glu Gln Lys Asp Phe Val Cys Asn Thr Lys
1               5                  10                  15
Gln Pro Gly Cys Pro Asn Val Cys Tyr Asp Glu Phe Phe Pro Val Ser
                20                  25                  30
His Val Arg
        35
```

<210> SEQ ID NO 41
<211> LENGTH: 35
<212> TYPE: PRT
<213> ORGANISM: Homo sapiens

<400> SEQUENCE: 41

```
Glu Arg Val Trp Gly Asp Glu Gln Lys Asp Phe Asp Cys Asn Thr Lys
1               5                  10                  15
Gln Pro Gly Cys Thr Asn Val Cys Tyr Asp Asn Tyr Phe Pro Ile Ser
                20                  25                  30
Asn Ile Arg
        35
```

<210> SEQ ID NO 42
<211> LENGTH: 35
<212> TYPE: PRT
<213> ORGANISM: Homo sapiens

<400> SEQUENCE: 42

```
Glu Arg Val Trp Ser Asp Asp His Lys Asp Phe Asp Cys Asn Thr Arg
1               5                  10                  15
Gln Pro Gly Cys Ser Asn Val Cys Phe Asp Glu Phe Phe Pro Val Ser
                20                  25                  30
His Val Arg
        35
```

<210> SEQ ID NO 43
<211> LENGTH: 35

```
<212> TYPE: PRT
<213> ORGANISM: Homo sapiens

<400> SEQUENCE: 43

Glu Ser Val Trp Gly Asp Glu Lys Ser Ser Phe Ile Cys Asn Thr Leu
1               5                   10                  15

Gln Pro Gly Cys Asn Ser Val Cys Tyr Asp Gln Phe Phe Pro Ile Ser
            20                  25                  30

His Val Arg
        35

<210> SEQ ID NO 44
<211> LENGTH: 35
<212> TYPE: PRT
<213> ORGANISM: Homo sapiens

<400> SEQUENCE: 44

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 45
<211> LENGTH: 35
<212> TYPE: PRT
<213> ORGANISM: Homo sapiens

<400> SEQUENCE: 45

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 46
<211> LENGTH: 35
<212> TYPE: PRT
<213> ORGANISM: Homo sapiens

<400> SEQUENCE: 46

Arg Pro Val Tyr Gln Asp Glu Gln Glu Arg Phe Val Cys Asn Thr Leu
1               5                   10                  15

Gln Pro Gly Cys Ala Asn Val Cys Tyr Asp Val Phe Ser Pro Val Ser
            20                  25                  30

His Leu Arg
        35

<210> SEQ ID NO 47
<211> LENGTH: 35
<212> TYPE: PRT
<213> ORGANISM: Homo sapiens

<400> SEQUENCE: 47

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30
```

His Val Arg
        35

<210> SEQ ID NO 48
<211> LENGTH: 35
<212> TYPE: PRT
<213> ORGANISM: Homo sapiens

<400> SEQUENCE: 48

Glu Asp Val Trp Gly Asp Glu Gln Ser Asp Phe Thr Cys Asn Thr Gln
1               5                   10                  15

Gln Pro Gly Cys Asx Asn Val Cys Tyr Asx Arg Ala Phe Pro Ile Ser
            20                  25                  30

His Ile Arg
        35

<210> SEQ ID NO 49
<211> LENGTH: 35
<212> TYPE: PRT
<213> ORGANISM: Homo sapiens

<400> SEQUENCE: 49

Glu Ala Ile Tyr Ser Asp Glu Gln Ala Lys Phe Thr Cys Asn Thr Arg
1               5                   10                  15

Gln Pro Gly Cys Asp Asn Val Cys Tyr Asp Ala Phe Ala Pro Leu Ser
            20                  25                  30

His Val Arg
        35

<210> SEQ ID NO 50
<211> LENGTH: 35
<212> TYPE: PRT
<213> ORGANISM: Homo sapiens

<400> SEQUENCE: 50

Glu Ser Ser Trp Gly Asp Glu Gln Ala Asp Phe Arg Cys Asp Thr Ile
1               5                   10                  15

Gln Pro Gly Cys Gln Asn Val Cys Thr Asp Gln Ala Phe Pro Ile Ser
            20                  25                  30

His Ile Arg
        35

<210> SEQ ID NO 51
<211> LENGTH: 36
<212> TYPE: PRT
<213> ORGANISM: Homo sapiens

<400> SEQUENCE: 51

Gly Glu Ser Ile Tyr Tyr Asp Glu Gln Ser Lys Phe Val Cys Asn Thr
1               5                   10                  15

Glu Gln Pro Gly Cys Glu Asn Val Cys Tyr Asp Ala Phe Ala Pro Leu
            20                  25                  30

Ser His Val Arg
        35

<210> SEQ ID NO 52
<211> LENGTH: 39
<212> TYPE: PRT
<213> ORGANISM: Homo sapiens

<400> SEQUENCE: 52

```
Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
            35

<210> SEQ ID NO 53
<211> LENGTH: 39
<212> TYPE: PRT
<213> ORGANISM: Homo sapiens

<400> SEQUENCE: 53

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
            35

<210> SEQ ID NO 54
<211> LENGTH: 39
<212> TYPE: PRT
<213> ORGANISM: Homo sapiens

<400> SEQUENCE: 54

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
            35

<210> SEQ ID NO 55
<211> LENGTH: 40
<212> TYPE: PRT
<213> ORGANISM: Homo sapiens

<400> SEQUENCE: 55

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys
            35                  40

<210> SEQ ID NO 56
<211> LENGTH: 39
<212> TYPE: PRT
<213> ORGANISM: Homo sapiens

<400> SEQUENCE: 56

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn
            35

<210> SEQ ID NO 57
```

```
<211> LENGTH: 39
<212> TYPE: PRT
<213> ORGANISM: Homo sapiens

<400> SEQUENCE: 57

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr
            35

<210> SEQ ID NO 58
<211> LENGTH: 32
<212> TYPE: PRT
<213> ORGANISM: Homo sapiens

<400> SEQUENCE: 58

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 59
<211> LENGTH: 32
<212> TYPE: PRT
<213> ORGANISM: Homo sapiens

<400> SEQUENCE: 59

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

<210> SEQ ID NO 60
<211> LENGTH: 38
<212> TYPE: PRT
<213> ORGANISM: Homo sapiens

<400> SEQUENCE: 60

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Ser Lys Ser
            35

<210> SEQ ID NO 61
<211> LENGTH: 38
<212> TYPE: PRT
<213> ORGANISM: Homo sapiens

<400> SEQUENCE: 61

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
            35

<210> SEQ ID NO 62
```

```
<211> LENGTH: 38
<212> TYPE: PRT
<213> ORGANISM: Homo sapiens

<400> SEQUENCE: 62

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr
            35

<210> SEQ ID NO 63
<211> LENGTH: 38
<212> TYPE: PRT
<213> ORGANISM: Homo sapiens

<400> SEQUENCE: 63

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr
            35

<210> SEQ ID NO 64
<211> LENGTH: 38
<212> TYPE: PRT
<213> ORGANISM: Homo sapiens

<400> SEQUENCE: 64

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
            35

<210> SEQ ID NO 65
<211> LENGTH: 38
<212> TYPE: PRT
<213> ORGANISM: Homo sapiens

<400> SEQUENCE: 65

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
            35

<210> SEQ ID NO 66
<211> LENGTH: 42
<212> TYPE: PRT
<213> ORGANISM: Homo sapiens

<400> SEQUENCE: 66

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30
```

-continued

Arg Pro Thr Glu Lys Thr Ile Phe Ile Ile
        35                  40

<210> SEQ ID NO 67
<211> LENGTH: 43
<212> TYPE: PRT
<213> ORGANISM: Homo sapiens

<400> SEQUENCE: 67

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr Val Phe Thr Val
        35                  40

<210> SEQ ID NO 68
<211> LENGTH: 42
<212> TYPE: PRT
<213> ORGANISM: Homo sapiens

<400> SEQUENCE: 68

Tyr Val Phe Tyr Phe Leu Tyr Asn Gly Tyr His Leu Pro Trp Val Leu
1               5                   10                  15

Lys Cys Gly Ile Asp Pro Cys Pro Asn Leu Val Asp Cys Phe Ile Ser
            20                  25                  30

Arg Pro Thr Glu Lys Thr Val Phe Thr Ile
        35                  40

<210> SEQ ID NO 69
<211> LENGTH: 43
<212> TYPE: PRT
<213> ORGANISM: Homo sapiens

<400> SEQUENCE: 69

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys Val Phe Thr Tyr
        35                  40

<210> SEQ ID NO 70
<211> LENGTH: 42
<212> TYPE: PRT
<213> ORGANISM: Homo sapiens

<400> SEQUENCE: 70

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys Thr Tyr
        35                  40

<210> SEQ ID NO 71
<211> LENGTH: 43
<212> TYPE: PRT
<213> ORGANISM: Homo sapiens

<400> SEQUENCE: 71

```
Leu Tyr Val Phe His Ser Phe Tyr Pro Lys Tyr Ile Leu Pro Pro Val
1               5                   10                  15

Val Lys Cys His Ala Asp Pro Cys Pro Asn Arg Val Asp Cys Phe Ile
                20                  25                  30

Ser Lys Pro Ser Glu Lys Asn Ile Phe Thr Leu
            35                  40
```

<210> SEQ ID NO 72
<211> LENGTH: 43
<212> TYPE: PRT
<213> ORGANISM: Homo sapiens

<400> SEQUENCE: 72

```
Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
                20                  25                  30

Ser Arg Pro Thr Glu Lys Thr Val Phe Thr Val
            35                  40
```

<210> SEQ ID NO 73
<211> LENGTH: 36
<212> TYPE: PRT
<213> ORGANISM: Homo sapiens

<400> SEQUENCE: 73

```
Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

Ile Phe Ile Ile
            35
```

<210> SEQ ID NO 74
<211> LENGTH: 36
<212> TYPE: PRT
<213> ORGANISM: Homo sapiens

<400> SEQUENCE: 74

```
Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

Ile Phe Ile Ile
            35
```

<210> SEQ ID NO 75
<211> LENGTH: 42
<212> TYPE: PRT
<213> ORGANISM: Homo sapiens

<400> SEQUENCE: 75

```
Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
                20                  25                  30

Arg Pro Thr Glu Lys Ser Leu Leu Met Leu
            35                  40
```

```
<210> SEQ ID NO 76
<211> LENGTH: 42
<212> TYPE: PRT
<213> ORGANISM: Homo sapiens

<400> SEQUENCE: 76

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
                20                  25                  30

Arg Pro Thr Glu Lys Thr Ile Phe Ile Ile
            35                  40

<210> SEQ ID NO 77
<211> LENGTH: 42
<212> TYPE: PRT
<213> ORGANISM: Homo sapiens

<400> SEQUENCE: 77

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
                20                  25                  30

Arg Pro Thr Glu Lys Thr Val Phe Leu Leu
            35                  40

<210> SEQ ID NO 78
<211> LENGTH: 41
<212> TYPE: PRT
<213> ORGANISM: Homo sapiens

<400> SEQUENCE: 78

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Ser Arg
                20                  25                  30

Pro Thr Glu Lys Asn Val Phe Ile Val
            35                  40

<210> SEQ ID NO 79
<211> LENGTH: 43
<212> TYPE: PRT
<213> ORGANISM: Homo sapiens

<400> SEQUENCE: 79

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
                20                  25                  30

Arg Pro Thr Glu Lys Thr Ile Phe Leu Leu Cys
            35                  40

<210> SEQ ID NO 80
<211> LENGTH: 45
<212> TYPE: PRT
<213> ORGANISM: Homo sapiens

<400> SEQUENCE: 80

Leu Gly Thr Ala Ala Glu Ser Ser Trp Gly Asp Glu Gln Ala Asp Phe
1               5                   10                  15

Arg Cys Asp Thr Ile Gln Pro Gly Cys Gln Asn Val Cys Thr Asp Gln
```

```
                 20                  25                  30
Ala Phe Pro Ile Ser His Ile Arg Phe Trp Val Leu Gln
             35                  40                  45
```

<210> SEQ ID NO 81
<211> LENGTH: 14
<212> TYPE: PRT
<213> ORGANISM: Homo sapiens

<400> SEQUENCE: 81

```
Leu Gly Thr Ala Ala Glu Ser Ser Trp Gly Asp Glu Gln Ala
1               5                   10
```

<210> SEQ ID NO 82
<211> LENGTH: 13
<212> TYPE: PRT
<213> ORGANISM: Homo sapiens

<400> SEQUENCE: 82

```
Asp Glu Gln Ala Asp Phe Arg Cys Asp Thr Ile Gln Pro
1               5                   10
```

<210> SEQ ID NO 83
<211> LENGTH: 13
<212> TYPE: PRT
<213> ORGANISM: Homo sapiens

<400> SEQUENCE: 83

```
Thr Ile Gln Pro Gly Cys Gln Asn Val Cys Thr Asp Gln
1               5                   10
```

<210> SEQ ID NO 84
<211> LENGTH: 13
<212> TYPE: PRT
<213> ORGANISM: Homo sapiens

<400> SEQUENCE: 84

```
Val Cys Thr Asp Gln Ala Phe Pro Ile Ser His Ile Arg
1               5                   10
```

<210> SEQ ID NO 85
<211> LENGTH: 13
<212> TYPE: PRT
<213> ORGANISM: Homo sapiens

<400> SEQUENCE: 85

```
Ala Phe Pro Ile Ser His Ile Arg Phe Trp Val Leu Gln
1               5                   10
```

<210> SEQ ID NO 86
<211> LENGTH: 47
<212> TYPE: PRT
<213> ORGANISM: Homo sapiens

<400> SEQUENCE: 86

```
Met Glu Val Gly Phe Ile Val Gly Gln Tyr Phe Ile Tyr Gly Ile Phe
1               5                   10                  15

Leu Thr Thr Leu His Val Cys Arg Arg Ser Pro Cys Pro His Pro Val
            20                  25                  30

Asn Cys Tyr Val Ser Arg Pro Thr Glu Lys Asn Val Phe Ile Val
            35                  40                  45
```

<210> SEQ ID NO 87

```
<211> LENGTH: 11
<212> TYPE: PRT
<213> ORGANISM: Homo sapiens

<400> SEQUENCE: 87

Met Glu Val Gly Phe Ile Val Gly Gln Tyr Phe
1               5                   10

<210> SEQ ID NO 88
<211> LENGTH: 12
<212> TYPE: PRT
<213> ORGANISM: Homo sapiens

<400> SEQUENCE: 88

Ile Val Gly Gln Tyr Phe Ile Tyr Gly Ile Phe Leu
1               5                   10

<210> SEQ ID NO 89
<211> LENGTH: 14
<212> TYPE: PRT
<213> ORGANISM: Homo sapiens

<400> SEQUENCE: 89

Gly Ile Phe Leu Thr Thr Leu His Val Cys Arg Arg Ser Pro
1               5                   10

<210> SEQ ID NO 90
<211> LENGTH: 12
<212> TYPE: PRT
<213> ORGANISM: Homo sapiens

<400> SEQUENCE: 90

Arg Arg Ser Pro Cys Pro His Pro Val Asn Cys Tyr
1               5                   10

<210> SEQ ID NO 91
<211> LENGTH: 12
<212> TYPE: PRT
<213> ORGANISM: Homo sapiens

<400> SEQUENCE: 91

Val Asn Cys Tyr Val Ser Arg Pro Thr Glu Lys Asn
1               5                   10

<210> SEQ ID NO 92
<211> LENGTH: 11
<212> TYPE: PRT
<213> ORGANISM: Homo sapiens

<400> SEQUENCE: 92

Ser Arg Pro Thr Glu Lys Asn Val Phe Ile Val
1               5                   10

<210> SEQ ID NO 93
<211> LENGTH: 46
<212> TYPE: PRT
<213> ORGANISM: Homo sapiens

<400> SEQUENCE: 93

Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
            20                  25                  30

Ala Phe Ala Pro Leu Ser His Val Arg Phe Trp Val Phe Gln
```

```
                      35                  40                  45
```

<210> SEQ ID NO 94
<211> LENGTH: 15
<212> TYPE: PRT
<213> ORGANISM: Homo sapiens

<400> SEQUENCE: 94

```
Leu Thr Ala Val Gly Gly Glu Ser Ile Tyr Tyr Asp Glu Gln Ser
1               5                   10                  15
```

<210> SEQ ID NO 95
<211> LENGTH: 13
<212> TYPE: PRT
<213> ORGANISM: Homo sapiens

<400> SEQUENCE: 95

```
Asp Glu Gln Ser Lys Phe Val Cys Asn Thr Glu Gln Pro
1               5                   10
```

<210> SEQ ID NO 96
<211> LENGTH: 13
<212> TYPE: PRT
<213> ORGANISM: Homo sapiens

<400> SEQUENCE: 96

```
Thr Glu Gln Pro Gly Cys Glu Asn Val Cys Tyr Asp Ala
1               5                   10
```

<210> SEQ ID NO 97
<211> LENGTH: 13
<212> TYPE: PRT
<213> ORGANISM: Homo sapiens

<400> SEQUENCE: 97

```
Val Cys Tyr Asp Ala Phe Ala Pro Leu Ser His Val Arg
1               5                   10
```

<210> SEQ ID NO 98
<211> LENGTH: 12
<212> TYPE: PRT
<213> ORGANISM: Homo sapiens

<400> SEQUENCE: 98

```
Ala Pro Leu Ser His Val Arg Phe Trp Val Phe Gln
1               5                   10
```

<210> SEQ ID NO 99
<211> LENGTH: 47
<212> TYPE: PRT
<213> ORGANISM: Homo sapiens

<400> SEQUENCE: 99

```
Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
            20                  25                  30

Asp Cys Phe Ile Ser Arg Pro Thr Glu Lys Thr Ile Phe Leu Leu
        35                  40                  45
```

<210> SEQ ID NO 100
<211> LENGTH: 11
<212> TYPE: PRT
<213> ORGANISM: Homo sapiens

<400> SEQUENCE: 100

Phe Glu Val Gly Phe Leu Ile Gly Gln Tyr Phe
1               5                   10

<210> SEQ ID NO 101
<211> LENGTH: 12
<212> TYPE: PRT
<213> ORGANISM: Homo sapiens

<400> SEQUENCE: 101

Leu Ile Gly Gln Tyr Phe Leu Tyr Gly Phe Gln Val
1               5                   10

<210> SEQ ID NO 102
<211> LENGTH: 14
<212> TYPE: PRT
<213> ORGANISM: Homo sapiens

<400> SEQUENCE: 102

Gly Phe Gln Val His Pro Phe Tyr Val Cys Ser Arg Leu Pro
1               5                   10

<210> SEQ ID NO 103
<211> LENGTH: 12
<212> TYPE: PRT
<213> ORGANISM: Homo sapiens

<400> SEQUENCE: 103

Ser Arg Leu Pro Cys His Pro Lys Ile Asp Cys Phe
1               5                   10

<210> SEQ ID NO 104
<211> LENGTH: 12
<212> TYPE: PRT
<213> ORGANISM: Homo sapiens

<400> SEQUENCE: 104

Ile Asp Cys Phe Ile Ser Arg Pro Thr Glu Lys Thr
1               5                   10

<210> SEQ ID NO 105
<211> LENGTH: 11
<212> TYPE: PRT
<213> ORGANISM: Homo sapiens

<400> SEQUENCE: 105

Ser Arg Pro Thr Glu Lys Thr Ile Phe Leu Leu
1               5                   10

<210> SEQ ID NO 106
<211> LENGTH: 10
<212> TYPE: PRT
<213> ORGANISM: Homo sapiens

<400> SEQUENCE: 106

Tyr Val Cys Ser Arg Leu Pro Cys His Pro
1               5                   10

<210> SEQ ID NO 107
<211> LENGTH: 11
<212> TYPE: PRT
<213> ORGANISM: Homo sapiens

<400> SEQUENCE: 107

```
Gln Val His Pro Phe Tyr Val Cys Ser Arg Leu
1               5                   10
```

<210> SEQ ID NO 108
<211> LENGTH: 13
<212> TYPE: PRT
<213> ORGANISM: Homo sapiens

<400> SEQUENCE: 108

```
Phe Glu Val Gly Phe Leu Ile Gly Gln Tyr Phe Leu Tyr
1               5                   10
```

<210> SEQ ID NO 109
<211> LENGTH: 12
<212> TYPE: PRT
<213> ORGANISM: Homo sapiens

<400> SEQUENCE: 109

```
Gly Gln Tyr Phe Leu Tyr Gly Phe Gln Val His Pro
1               5                   10
```

<210> SEQ ID NO 110
<211> LENGTH: 12
<212> TYPE: PRT
<213> ORGANISM: Homo sapiens

<400> SEQUENCE: 110

```
Gly Phe Gln Val His Pro Phe Tyr Val Cys Ser Arg
1               5                   10
```

<210> SEQ ID NO 111
<211> LENGTH: 12
<212> TYPE: PRT
<213> ORGANISM: Homo sapiens

<400> SEQUENCE: 111

```
Ala Val Gly Gly Glu Ser Ile Tyr Tyr Asp Glu Gln
1               5                   10
```

<210> SEQ ID NO 112
<211> LENGTH: 12
<212> TYPE: PRT
<213> ORGANISM: Homo sapiens

<400> SEQUENCE: 112

```
Tyr Asp Glu Gln Ser Lys Phe Val Cys Asn Thr Glu
1               5                   10
```

<210> SEQ ID NO 113
<211> LENGTH: 12
<212> TYPE: PRT
<213> ORGANISM: Homo sapiens

<400> SEQUENCE: 113

```
Asn Thr Glu Gln Pro Gly Cys Glu Asn Val Cys Tyr
1               5                   10
```

<210> SEQ ID NO 114
<211> LENGTH: 12
<212> TYPE: PRT
<213> ORGANISM: Homo sapiens

<400> SEQUENCE: 114

```
Cys Tyr Asp Ala Phe Ala Pro Leu Ser His Val Arg
```

```
1               5                   10

<210> SEQ ID NO 115
<211> LENGTH: 12
<212> TYPE: PRT
<213> ORGANISM: Homo sapiens

<400> SEQUENCE: 115

Phe Ala Pro Leu Ser His Val Arg Phe Trp Val Phe
1               5                   10

<210> SEQ ID NO 116
<211> LENGTH: 5
<212> TYPE: PRT
<213> ORGANISM: Homo sapiens

<400> SEQUENCE: 116

Leu Ile Gly Gln Tyr
1               5

<210> SEQ ID NO 117
<211> LENGTH: 5
<212> TYPE: PRT
<213> ORGANISM: Homo sapiens

<400> SEQUENCE: 117

Gln Val His Pro Phe
1               5

<210> SEQ ID NO 118
<211> LENGTH: 5
<212> TYPE: PRT
<213> ORGANISM: Homo sapiens

<400> SEQUENCE: 118

Tyr Val Cys Ser Arg
1               5

<210> SEQ ID NO 119
<211> LENGTH: 5
<212> TYPE: PRT
<213> ORGANISM: Homo sapiens

<400> SEQUENCE: 119

Ser Arg Leu Pro Cys
1               5

<210> SEQ ID NO 120
<211> LENGTH: 5
<212> TYPE: PRT
<213> ORGANISM: Homo sapiens

<400> SEQUENCE: 120

Leu Pro Cys His Pro
1               5

<210> SEQ ID NO 121
<211> LENGTH: 5
<212> TYPE: PRT
<213> ORGANISM: Homo sapiens

<400> SEQUENCE: 121

Gly Glu Ser Ile Tyr
1               5
```

```
<210> SEQ ID NO 122
<211> LENGTH: 6
<212> TYPE: PRT
<213> ORGANISM: Homo sapiens

<400> SEQUENCE: 122

Tyr Asp Glu Gln Ser Lys
1               5

<210> SEQ ID NO 123
<211> LENGTH: 6
<212> TYPE: PRT
<213> ORGANISM: Homo sapiens

<400> SEQUENCE: 123

Ser Lys Phe Val Cys Asn
1               5

<210> SEQ ID NO 124
<211> LENGTH: 8
<212> TYPE: PRT
<213> ORGANISM: Homo sapiens

<400> SEQUENCE: 124

Thr Glu Gln Pro Gly Cys Glu Asn
1               5

<210> SEQ ID NO 125
<211> LENGTH: 8
<212> TYPE: PRT
<213> ORGANISM: Homo sapiens

<400> SEQUENCE: 125

Val Cys Tyr Asp Ala Phe Ala Pro
1               5

<210> SEQ ID NO 126
<211> LENGTH: 10
<212> TYPE: PRT
<213> ORGANISM: Homo sapiens

<400> SEQUENCE: 126

Leu Ser His Val Arg Phe Trp Val Phe Gln
1               5                   10
```

US 8,956,868 B2

INDUCED PLURIPOTENT STEM CELLS PRODUCED WITH A CONNEXIN INHIBITOR AND A TGF-β SIGNALING INHIBITOR

CROSS-REFERENCE TO RELATED APPLICATIONS

This patent application claims the benefit of U.S. Provisional Patent Application No. 61/427,354, filed Dec. 27, 2010, which is incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted on Dec. 27, 2011 and identified as follows: 33,177 bytes ASCII (Text) file named "709596SequenceListing.txt," created Dec. 27, 2011.

TECHNICAL FIELD

The present invention relates to iPS cells (induced pluripotent stem cells) and a method for producing the same. The present invention also relates to an iPS cell inducer, a medium for inducing iPS cells, and a kit for inducing iPS cells.

BACKGROUND ART iPS cells are also referred to as artificial pluripotent stem cells or induced pluripotent stem cells, which are cells achieving pluripotent differentiation ability equivalent to that of embryonic stem (ES) cells.

Cells having pluripotent differentiation ability, such as ES cells and iPS cells, have the ability to differentiate into all organs and tissues constituting an organism. Accordingly, these cells are expected, to be a highly effective means for reproducing organs, blood, bone marrow, tissue, etc., that are damaged by some diseases.

However, blood, bone marrow, tissue, organs, and other biological materials obtained from ES cells may cause transplant rejection. It is essential to solve such immunological problems, and there are also ethical problems. Conversely, iPS cells can be produced using a patient's own somatic cells; hence, there are neither immunological rejection problems nor ethical problems.

Professor Shinya Yamanaka and his group have succeeded in producing iPS cells by introducing genes of four types of reprogramming factors Oct3/4, Sox2, Klf4, and c-Myc (so-called Yamanaka factors) into mouse fibroblasts (NPL 1 and NPL 2); however, clinical application of the iPS cells has the following problems:

1. There is a possibility that foreign genes, such as bacteria DNA, may be integrated into the genome of the host cell.
2. iPS cells produced by conventional methods have safety problems because they become cancerous at a constant frequency.
3. iPS cells produced by overexpression of foreign genes have unexpected influences, other than pluripotency.

CITATION LIST

Non-Patent Literature

NPL 1: Takahashi et al., Cell 2006, 126: 663-676.
NPL 2: Okita et al., Nature 2007, 448: 313-317.

SUMMARY OF THE INVENTION

Problems to be Solved by the Invention

An object of the present invention is to provide safe iPS cells that have no risk of becoming cancerous.

Means for Solving the Problems

The present inventors conducted research in view of the above problems, and surprisingly found, that iPS cells could be established, without introducing genes, by reacting cells with a connexin inhibitor and a TGF-β signaling inhibitor.

The present invention provides iPS cells, a method for producing the same, an iPS cell inducer, a medium for inducing iPS cells, and a kit for inducing iPS cells, as described below.

Item 1. A method for producing iPS cells, comprising reacting cells with at least one connexin inhibitor and at least one TGFβ signaling inhibitor.
Item 2. The method according to Item 1, wherein the connexin inhibitor is a connexin 43 inhibitor.
Item 3. The method according to Item 1 or 2, wherein the connexin inhibitor is siRNA, shRNA, miRNA, antisense RNA, peptide, antibody, or ribozyme against connexin, or an expression vector that can release RNA molecules thereof in the cells.
Item 4. The method according to any one of Items 1 to 3, wherein the TGF-β signaling inhibitor is a TGF-β receptor I inhibitor.
Item 5. The method according to any one of Items 1 to 4, wherein the TGF-β receptor inhibitor is SB-431542, A-83-01, or ALK5 inhibitor.
Item 6. iPS cells comprising at least one connexin inhibitor.
Item 7. The iPS cells according to Item 6, wherein the connexin inhibitor is a connexin 43 inhibitor.
Item 8. The iPS cells according to Item 6 or 7, wherein the connexin inhibitor is siRNA, shRNA, miRNA, antisense RNA, peptide, antibody, or ribozyme against connexin, or an expression vector that can release RNA molecules thereof in the cells.
Item 9. An iPS cell inducer comprising at least one inhibitor selected from the group consisting of connexin inhibitors and TGF-β signaling inhibitors.
Item 10. A medium for inducing iPS cells, comprising at least one inhibitor selected from the group consisting of connexin inhibitors and TGF-β signaling inhibitors.
Item 11. A kit for inducing iPS cells, comprising at least one inhibitor selected from, the group consisting of connexin inhibitors and TGF-β signaling inhibitors.

Effects of the Invention

The method of the present invention can produce iPS cells that have a great advantage in their practical use for human, because introduction of foreign genes (particularly, oncogenes) is not required, any characteristics other than the iPS cells are not changed because no virus is used, and the iPS cells are so safe that they have very low risk of becoming cancerous or being infected.

The following four points regarding the iPS cells of the present invention have been confirmed:

1. Pluripotent cell marker factor expression is maintained, at the genetic and protein levels.
2. Subcutaneous implantation of the iPS cells in mice leads to teratoma formation and induces differentiation into all three germ layers, including gland, cartilage, and neural tissues.

3. Embryoid bodies are formed, and are able to differentiate into endothelial cells, neural cells, and cardiomyocytes depending on differentiation-inducing conditions. The differentiated cardiomyocytes function physiologically.

4. Chimeric mice can be produced.

In addition, the iPS cells of the present invention allow the production of germ lines.

Accordingly, the iPS cells provided by the present invention are very excellent in producing biological materials for use in, for example, regenerative medicine.

MODE FOR CARRYING OUT THE INVENTION

Figure 1:
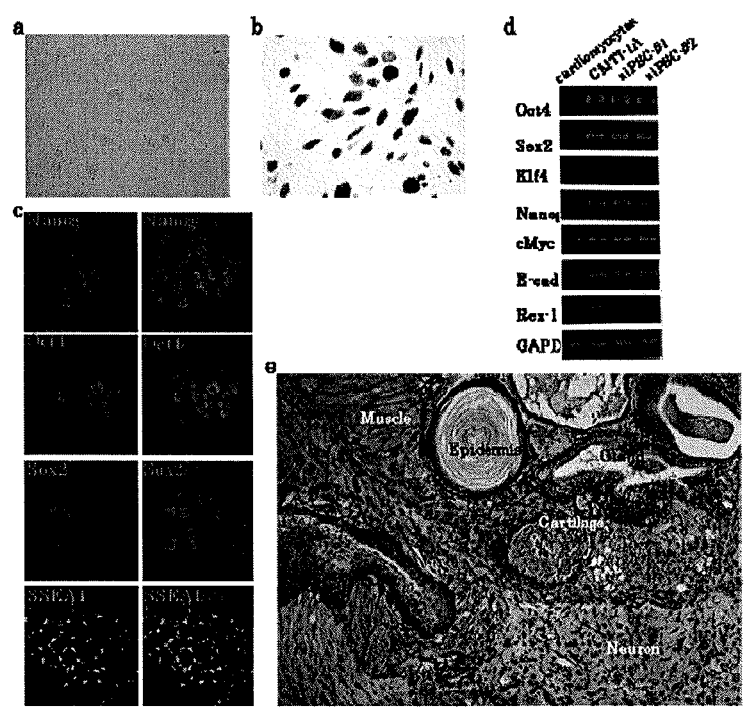
FIG. 1 shows the results regarding cells obtained in the examples of the present invention.
  a. The morphology of siPSCs is similar to that of mouse ES cells.
  b. ALP activity of siPSCs was observed.
  c. Expression was confirmed at the protein level by immunostaining using various anti-pluripotency marker antibodies (Nanog, Oct4, Sox2, and SSEA1).
  d. The expression of various anti-pluripotency marker genes was confirmed at the gene level by RT-PCR.
  e. When the cells were implanted subcutaneously in SCID mice, teratomas were formed; and gland, cartilage/muscle, and nerve/epithelium were confirmed.

In the present specification, the term "iPS cells" refers to cells that have achieved pluripotent differentiation ability, which are also called artificial pluripotent stem cells or induced pluripotent stem cells. The iPS cells obtained in the present invention are able to differentiate into all of endodermal cells, ectodermal cells, and mesodermal cells (see FIG. 1), and allow the production of chimeric mice (FIG. 3) and germ lines.

The term "connexin (Cx)" is a generic name of proteins involved in gap junction, and they are named, for example, Cx43 (43 kDa), depending on their molecular weight. Specific examples of connexins include Cx26, Cx30, Cx31, Cx32, Cx36, Cx37, Cx40, Cx43, Cx45, Cx50, etc. More than 20 types of connexins are currently known. The target connexins for inhibition in the present invention also include connexins to be discovered in the future. The type and expression of connexins are described in detail in a review paper (Oyamada et al., BBA, 2005, 1719: 6-23), and the description thereof is incorporated herein by reference. The type and expression site of connexins are summarized in the following table.

TABLE 1

| Tissue or cell type | Expressed connexin | |
|---|---|---|
| | Human | Mouse |
| — | hCx23 | mCx23 |
| — | hCx25 | — |
| Breast, cochlea, placenta, hepatocyte, skin, pancreas, kidney, intestine | hCx26 | mCx26 |

TABLE 1-continued

| Tissue or cell type | Expressed connexin | |
|---|---|---|
| | Human | Mouse |
| Brain, cochlea, skin | hCx30 | mCx30 |
| Brain, spinal cord, Schwann cells | hCx30.2 | mCx29 |
| Skin, kidney | hCx30.3 | mCx30.3 |
| Cochlea, placenta, skin | hCx31 | mCx31 |
| Skin | hCx31.1 | mCx31.1 |
| — | hCx31.9 | mCx30.2 |
| Hepatocyte, secretory acinar cells, Schwann cells | hCx32 | mCx32 |
| Sertoli cells | — | mCx33 |
| Neurons, pancreatic β-cells | hCx36 | mCx36 |
| Endothelium, granulosa cells, lung, skin | hCx37 | mCx37 |
| Cardiac conduction system, endothelium, lung | hCx40 | mCx40 |
| — | hCx40.1 | mCx39 |
| Many cell types | hCx43 | mCx43 |
| Cardiac conduction system, smooth muscle cells, neurons | hCx45 | mCx45 |
| Lens | hCx46 | mCx46 |
| Brain, spinal cord | hCx47 | mCx47 |
| Lens | hCx50 | mCx50 |
| — | hCx59 | — |
| Retinal horizontal cells | hCx62 | mCx57 |

The table above shows connexins mainly expressed in tissues. In the present invention, it is preferable to inhibit connexins mainly expressed in target cells. For example, in the ventricle muscle in which Cx43 is highly expressed, it is preferable to inhibit Cx43. In addition, Cx45 is also expressed in the ventricle muscle; Cx45 may be inhibited, or Cx43 and Cx45 may be inhibited at the same time. Preferred connexins to be inhibited are connexins 26, 32, 43, 45, etc., that are expressed in many cell types. Particularly preferred is connexin 43. The amino acid sequences of connexin 43 are known, and some examples are shown below.

TABLE 2

| Origin of Cx43 | Database accession number of gene/amino acid sequence |
|---|---|
| Human | NM_000165 |
| Rat | NM_000567 |
| Mouse | NM_010288 |
| Monkey | AB169817 |

Depending on the animal species of iPS cells, corresponding connexin inhibitors can be used.

The functions of connexin inhibitors are, for example, inhibition of connexin gene expression in cells (inhibition of transcription or translation), functional inhibition due to complex formation with intracellular connexins (proteins), and the like. Specific examples of connexin inhibitors include siRNA, shRNA, miRNA, antisense RNA, peptide, antibody, or ribozyme against connexins, and expression vectors that can release RNA molecules thereof in cells. Preferred among these are siRNA, shRNA, miRNA, antisense RNA, and ribozyme; and more preferred are siRNA, shRNA, and miRNA. Since they have different sequences depending on the type of connexin, the source of the cells, etc., it is necessary to select suitable sequences. Those skilled in the art can easily design or select suitable sequences of siRNA, shRNA, miRNA, antisense RNA, peptide, ribozyme, or expression vectors that can release RNA molecules thereof in cells. For example, preferred examples of siRNA against connexin 43 in human (the same sequences are applicable to monkey) are as follows:

Sense:
(SEQ ID NO: 1)
5'-CAA UUC UUC UUG CCG CAA TT-3'

Antisense:
(SEQ ID NO: 2)
5'-UUG CCG CAA GAA GAA UUG TT-3'

As connexin inhibitors, glycosaminoglycan having a sulfuric acid group (Japanese Unexamined Patent Publication No. 2003-119146; the description thereof is incorporated herein by reference) can also be used.

In one embodiment, "connexin inhibitors" are compounds that affect or modulate a connexin, a connexin hemichannel (connexon), or the cell proliferative activity of a connexin. Connexin inhibitors include, without limitation, antisense compounds (e.g., antisense polynucleotides), RNAi and siRNA compounds, antibodies and binding fragments thereof, and peptides and polypeptides (including "peptidomimetics" and peptide analogs). A preferred connexin inhibitor is a connexin 43 inhibitor. Exemplary connexin inhibitors are described in further detail herein.

In one embodiment, the connexin inhibitors of the present invention can modulate or affect the transport of molecules into and out of cells (e.g., blocking, inhibition, or downregulation).

Certain connexin inhibitors provide downregulation of connexin expression, for example, by downregulation of mRNA transcription or translation, or decrease or inhibit a connexin protein, a connexin hemichannel or cell proliferative activity (Asazuma-Nakamura et al., Exp Cell Res., 2009, 315: 1190-1199; Nakano et al., Invest Ophthalmol Vis Sci., 2007, 49: 93-104; Zhang et al., Oncogene, 2001, 20: 4138-4149).

Examples of connexin inhibitors include agents that decrease or inhibit expression or function of connexin mRNA and/or protein, or that decrease a connexin, a connexin hemichannel or cell proliferative activity. Connexin inhibitors include anti-connexin polynucleotides, such as antisense polynucleotides and other polynucleotides (e.g., polynucleotides having siRNA or ribozyme functionalities), as well as antibodies and binding fragments thereof, and peptides and polypeptides (including peptidomimetics and peptide analogs that modulate hemichannel or cell proliferative activity).

Anti-Connexin Polynucleotides

Anti-connexin polynucleotides include connexin antisense polynucleotides as well as polynucleotides having functionalities that enable them to downregulate connexin expression. Other suitable anti-connexin polynucleotides include RNAi polynucleotides, siRNA polynucleotides, and shRNA polynucleotides.

Synthesis of antisense polynucleotides and other anti-connexin polynucleotides (RNAi, siRNA, and ribozyme polynucleotides as well as polynucleotides having modified and mixed backbones) is known to those of skill in the art. See, e.g., Stein C. A. and Krieg A. M. (Eds.), Applied Antisense Oligonucleotide Technology, 1998 (Wiley-hiss). Methods of synthesizing antibodies and binding fragments as well as peptides and polypeptides (including peptidomimetics and peptide analogs) are known to those of skill in the art. See, e.g., Lihu Yang et al., Proc. Natl. Acad. Sci. U.S.A., 1; 95(18): 10836-10841 (Sep. 1, 1998); Harlow and Lane (1988) "Antibodies: A Laboratory Manual" Cold Spring Harbor Publications, New York; Harlow and Lane (1999) "Using Antibodies" A Laboratory Manual, Cold Spring Harbor Publications, New York.

According to one aspect, the downregulation of connexin expression is based generally upon the use of antisense polynucleotides (such as DNA or RNA polynucleotides), and more particularly upon the use of antisense oligodeoxynucleotides (ODN). These polynucleotides (e.g., ODN) target the connexin protein(s) to be downregulated. Typically, the polynucleotides are single-stranded, but may be double-stranded.

The antisense polynucleotide may inhibit transcription and/or translation of a connexin. Preferably, the polynucleotide is a specific inhibitor of transcription and/or translation from the connexin gene or mRNA, and does not inhibit transcription and/or translation from other genes or mRNAs. The product may bind to the connexin gene or mRNA either (i) 5' to the coding sequence, and/or (ii) to the coding sequence, and/or (iii) 3' to the coding sequence.

The antisense polynucleotide is generally antisense to a connexin mRNA. Such a polynucleotide may be capable of hybridizing to the connexin mRNA, and may thus inhibit the expression of connexin by interfering with one or more aspects of connexin mRNA metabolism (including transcription, mRNA processing, mRNA transport from the nucleus, translation or mRNA degradation). The antisense polynucleotide typically hybridizes to the connexin mRNA to form a duplex that can cause direct inhibition of translation and/or destabilization of the mRNA. Such a duplex may be susceptible to degradation by nucleases.

The antisense polynucleotide may hybridize to all or part of the connexin mRNA. Typically, the antisense polynucleotide hybridizes to the ribosome binding region or the coding region of the connexin mRNA. The polynucleotide may be complementary to all of or a region of the connexin mRNA. For example, the polynucleotide may be the exact complement of all or a part of connexin mRNA. However, absolute complementarity is not required, and polynucleotides that have sufficient complementarity to form a duplex having a melting temperature of greater than about 20° C., 30° C. or 40° C. under physiological conditions are particularly suitable for use in the present invention.

Thus, the polynucleotide is typically a homologue of a sequence complementary to the mRNA. The polynucleotide may be a polynucleotide that hybridizes to the connexin mRNA under conditions of medium to high stringency, such as 0.03 M sodium chloride and 0.03 M sodium citrate at from about 50° C. to about 60° C.

For certain aspects, suitable polynucleotides are typically from about 6 to 40 nucleotides in length. Preferably, a polynucleotide may be from about 12 to about 35 nucleotides in length, or more preferably from about 18 to about 32 nucleotides in length. According to another aspect, the polynucleotide may be at least about 40, for example, at least about 60 or at least about 80 nucleotides in length; and up to about 100, about 200, about 300, about 400, about 500, about 1,000, about 2,000 or about 3,000 or more nucleotides in length.

The connexin protein or proteins targeted by the polynucleotide will be dependent upon the site at which downregulation is to be effected. The connexin is a connexin that naturally occurs in a human or animal in one aspect, or naturally occurs in the tissue in which connexin expression or activity is to be decreased. The connexin gene (including coding sequence) generally has homology with the coding sequence of one or more of the specific connexins mentioned herein, such as homology with the connexin 43 coding sequence. The connexin is typically an α or β connexin. Preferably, the connexin is an α connexin and is expressed in the cells used as the starting material for iPS.

Some connexin proteins are, however, more ubiquitous than others in terms of distribution in tissue. One of the most widespread is connexin 43. Polynucleotides targeted to connexin 43 are particularly suitable for use in the present invention. In other aspects, other connexins are targeted.

Anti-connexin polynucleotides include connexin antisense polynucleotides as well as polynucleotides having functionalities that enable them to downregulate connexin expression. Other suitable anti-connexin polynucleotides include RNAi polynucleotides, shRNA polynucleotides, and siRNA polynucleotides.

In one preferred aspect, the antisense polynucleotides are targeted to the mRNA of only one connexin protein. Most preferably, this connexin protein is connexin 43. In other aspects, the connexin protein is connexin 26, 30, 31.1, 32, 36, 37, 40, or 45. In still other aspects, the connexin protein is connexin 30.3, 31, 40.1, or 47. These are examples of human connexin proteins. In the case of other animal species, mRNA of the corresponding connexin is targeted.

It is also contemplated that polynucleotides targeted to separate connexin proteins may be used in combination (e.g., 1, 2, 3, 4 or more different connexins may be targeted). For example, polynucleotides targeted to connexin 4.3, and one or more other members of the connexin family (such as connexins 26, 30, 30.3, 31.1, 32, 36, 37, 40, 40.1, 45, and 47) can be used in combination.

Alternatively, the antisense polynucleotides may be part of compositions that may comprise polynucleotides to more than one connexin protein. Preferably, one of the connexin proteins to which polynucleotides are directed is connexin 43. Other connexin proteins to which oligodeoxynucleotides are directed may include, for example, connexins 26, 30, 30.3, 31.1, 32, 36, 37, 40, 40.1, 45, and 47. Suitable exemplary polynucleotides (and ODNs) directed to various connexins are set forth in SEQ ID NOs: 3 to 14.

Individual antisense polynucleotides may be specific to a particular connexin, or may target 1, 2, 3 or more different connexins. Specific polynucleotides will generally target sequences in the connexin gene or mRNA that are not conserved between connexins, whereas non-specific polynucleotides will target conserved sequences for various connexins.

The polynucleotides for use in the invention may suitably be unmodified phosphodiester oligomers. Such oligodeoxynucleotides may vary in length. A 30 mer polynucleotide has been found to be particularly suitable.

Many aspects of the invention are described with reference to oligodeoxynucleotides. However, it is understood that other suitable polynucleotides (such as RNA polynucleotides) may be used in these aspects.

The antisense polynucleotides may be chemically modified. This may enhance their resistance to nucleases and may enhance their ability to enter cells. For example, phosphorothioate oligonucleotides may be used. Other deoxynucleotide analogs include methylphosphonates, phosphoramidates, phosphorodithioates, N3'P5'-phosphoramidates and oligoribonucleotide phosphorothioates, and their 2'-O-alkyl analogs and 2'-O-methylribonucleotide methylphosphonates. Alternatively, mixed backbone oligonucleotides ("MBOs") may be used. MBOs contain segments of phosphorothioate oligodeoxynucleotides and appropriately placed segments of modified oligodeoxy- or oligoribonucleotides. MBOs have segments of phosphorothioate linkages and segments of other modified oligonucleotides, such as methylphosphonate, which is non-ionic, and very resistant to nucleases or 2'-O-alkyloligoribonucleotides. Methods of preparing modified backbone and mixed backbone oligonucleotides are known in the art.

The precise sequence of the antisense polynucleotide used in the invention will depend upon the target connexin protein.

In one embodiment, suitable connexin antisense polynucleotides can include polynucleotides (SEQ ID NOs: 3 to 14).

Suitable polynucleotides for the preparation of the combined polynucleotides described herein include, for example, polynucleotides to Connexin Cx43 and polynucleotides for connexins 26, 30, 31.1, 32 and 37.

Although the precise sequence of the antisense polynucleotide used in the invention will depend upon the target connexin protein, for connexin 43, antisense polynucleotides having the following sequences have been found to be particularly suitable:

```
                                           (SEQ ID NO: 3)
    GTA ATT GCG GCA AGA AGA ATT GTT TCT GTC;

(SEQ ID NO: 4)
    GTA ATT GCG GCA GGA GGA ATT GTT TCT GTC;
    and (SEQ ID NO: 5)
    GGC AAG AGA CAC CAA AGA CAC TAC CAG CAT.
```

For example, suitable antisense polynucleotides for connexins 26, 31.1 and 32 have the following sequences:

```
                                           (SEQ ID NO: 6)
    5' TCC TGA GCA ATA CCT AAC GAA CAA ATA
    (connexin 26);

(SEQ ID NO: 11)
    5' CGT CCG AGC CCA GAA AGA TGA GGT C
    (connexin 31.1);
    and (SEQ ID NO: 14)
    5' TTT CTT TTC TAT GTG CTG TTG GTG A
    (connexin 32).
```

Other connexin antisense polynucleotide sequences useful according to the methods of the present invention include:

```
                                           (SEQ ID NO: 7)
    5' CAT CTC CTT GGT GCT CAA CC 3'
    (connexin 37);

(SEQ ID NO: 8)
    5' CTG AAG TCG ACT TGG CTT GG 3'
    (connexin 37);

(SEQ ID NO: 9)
    5' CTC AGA TAG TGG CCA GAA TGC 3'
    (connexin 30);

(SEQ ID NO: 10)
    5' TTG TCC AGG TGA CTC CAA GG 3'
    (connexin 30);

(SEQ ID NO: 12)
    5' AGA GGC GCA CGT GAG ACA C 3'
    (connexin 31.1);
    and (SEQ ID NO: 13)
    5' TGA AGA CAA TGA AGA TGT T 3'
    (connexin 31.1).
```

Polynucleotides (including ODNs) directed to connexin proteins can be selected in terms of their nucleotide sequence by any convenient and conventional approach. For example, the computer programs MacVector and OligoTech (from Oligos Etc., Eugene, Oreg., USA) can be used. Once selected, the ODNs can be synthesized using a DNA synthesizer.

Polynucleotide Homologues

For example, the polynucleotide may be a homologue of a complement to a sequence in connexin mRNA. Such a polynucleotide typically has at least about 70% homology, preferably at least about 80%, at least about 90%, at least about 95%, at least about 97%, at least about 98% or at least about 99% homology with the relevant sequence, for example, over a region of more than at least about 15, at least about 20, at least about 40, at least about 100 contiguous nucleotides (of the homologous sequence).

Homology may be calculated based on any method in the art. For example, the UWGCG Package provides the BEST-FIT program, which can be used to calculate homology (for example, used on its default settings) (Devereux et al. (1984) Nucleic Acids Research 12, p 387-395). The PILEUP and BLAST algorithms can be used to calculate homology or line up sequences (typically on their default settings), for example, as described in Altschul, S. F. (1993) J Mol Evol 36: 290-300; Altschul, S. F. et al. (1990) J Mol Biol 215: 403-10.

Software for performing BLAST analyses is publicly available through the National Center for Biotechnology Information (http://www.ncbi.nlm.nih.gov/). This algorithm involves first identifying high-scoring sequence pairs (HSPs) by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when:

the cumulative alignment score falls off by the quantity X from its maximum achieved value;

the cumulative score goes to zero or below, due to the accumulation of one or more negative-scoring residue alignments; or the end of either sequence is reached.

The BLAST algorithm parameters W, T and X determine the sensitivity and speed of the alignment. The BLAST program uses as defaults a word length (W), the BLOSUM62 scoring matrix (Henikoff and Henikoff (1992) Proc. Natl. Acad. Sci USA 89: 10915-10919), alignments (B) of 50, expectation (E) of 10, M=5, N=4, and a comparison of both strands.

The BLAST algorithm performs a statistical analysis of the similarity between two sequences. See, e.g., Karlin and Altschul (1993) Proc. Natl. Acad. Sci. USA 90: 5873-5787. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to a second sequence is less than about 1, preferably less than about 0.1, more preferably less than about 0.01, and most preferably less than about 0.001.

The homologous sequence typically differs from the relevant sequence by at least about 2, 5, 10, 15, 20 or more mutations (which may be substitutions, deletions or insertions). These mutations may be measured across any of the regions mentioned above in relation to calculating homology.

The homologous sequence typically hybridizes selectively to the original sequence at a level significantly above background. Selective hybridization is typically achieved using conditions of medium to high stringency (for example, 0.03M sodium chloride and 0.03 M sodium citrate at from, about 50° C. to about 60° C.). However, such hybridization may be carried out under any suitable conditions known in the art (see Sambrook et al. (1989), Molecular Cloning: A Laboratory Manual). For example, if high stringency is required, suitable conditions include 0.2×SSC at 60° C. If lower stringency is required, suitable conditions include 2×SSC at 60° C.

Peptide and Polypeptide Connexin Inhibitor

Binding proteins (including peptides, peptidomimetics, antibodies, antibody fragments, and the like) are also suitable inhibitors.

Binding proteins include, for example, monoclonal antibodies, polyclonal antibodies, antibody fragments (including, for example. Fab, F(ab')$_2$ and Fv fragments); single chain antibodies; single chain Fvs; and single chain binding molecules (those comprising, for example, a binding domain, hinge, CH2 and CH3 domains), recombinant antibodies and antibody fragments that are capable of binding an antigenic determinant (i.e., that portion of a molecule, generally referred to as an epitope) that makes contact with a particular antibody or other binding molecule. These binding proteins (including antibodies, antibody fragments, and so on) may be chimeric or humanized, or otherwise made to be less immunogenic in the subject to whom, they are to be administered, and may be synthesized, produced recombinantly, or produced in expression libraries. Any binding molecule known in the art or later discovered is envisioned, such as those referenced herein, and/or described in greater detail in the art. For example, binding proteins include not only antibodies and the like, but also ligands, receptors, peptidomimetics, or other binding fragments or molecules (for example, produced by phage display) that bind to a target (e.g., connexin or associated molecules).

Binding molecules will generally have a desired specificity (including, but not limited, to, binding specificity) and desired affinity. Affinity, for example, may be a Ka of greater than or equal to about $10^4 M^{-1}$, greater than or equal to about $10^6 M^{-1}$, greater than or equal to about $10^7 M^{-1}$, greater than or equal to about $10^8 M^{-1}$. Affinities of even greater than about $10^8 M^{-1}$ (affinities equal to or greater than about $10^9 M^{-1}$, about $10^{10} M^{-1}$, about $10^{11} M^{-1}$, and about $10^{12} M^{-1}$) are suitable. Affinities of binding proteins according to the present invention can be readily determined using conventional techniques (for example, those described by Scatchard et al., 1949 Ann. NY. Acad. Sci. 51: 660).

By using data, obtained from hydropathy plots, it has been proposed that a connexin contains four-transmembrane-spanning regions and two short extra-cellular loops. The positioning of the first, and second extracellular regions of connexin was further characterized by the reported production of anti-peptide antibodies used for immunolocalization of the corresponding epitopes on split gap junctions. Goodenough D. A., J Cell Biol 107: 1817-1824 (1988); Meyer R. A., J Cell Biol 119: 179-189 (1992).

Connexin inhibitors include peptides comprising an amino acid sequence corresponding to a transmembrane region (e.g., 1st to 4th) of a connexin (e.g., connexins 45, 43, 26, 30, 31.1, and 37). Connexin inhibitors may comprise a peptide comprising an amino acid sequence corresponding to a portion of a transmembrane region of a connexin 45. Connexin inhibitors include a peptide having an amino acid sequence that comprises about 5 to 20 contiguous amino acids of accession number: AAA60458, a peptide having an amino acid sequence that comprises about 8 to 15 contiguous amino acids of accession number: AAA60458, or a peptide having an amino acid sequence that comprises about 11 to 13 contiguous amino acids of accession number: AAA60458. Other embodiments are directed to a connexin inhibitor that is a peptide having an amino acid sequence that comprises at least about 5, at least about 6, at least about 7, at least about 8, at least about 9, at least about 10, at least about 11, at least, about 12, at least about 13, at least about 14, at least about 15, at least about 20, at least about 25, or at least about 30 contiguous amino acids of accession number: AAA60458. In certain connexin inhibitors provided herein, the extracellular domains of connexin 45 corresponding to the amino acids at positions 46-75 and 199-228 of accession number: AAA60458 may be used to develop the particular peptide sequences. Certain peptides described herein have an amino acid sequence corresponding to the regions at positions 46-75 and 199-228 of accession number: AAA60458. The peptides need not have an amino acid sequence identical to those portions of accession number: AAA60458, and conservative amino acid changes may be made such that the peptides retain binding activity or functional activity. Alternatively, the peptide may target regions of the connexin protein other than the extracellular domains (e.g., the portions of accession number: AAA60458 not corresponding to positions 46-75 and 199-228).

Also, suitable connexin inhibitors comprise a peptide comprising an amino acid sequence corresponding to a portion of a transmembrane region of a connexin 43. Connexin inhibitors include peptides having an amino acid sequence that comprises about 5 to 20 contiguous amino acids of accession number: NP_034418, peptides having an amino acid sequence that comprises about 8 to 15 contiguous amino acids of accession number: NP_034418, or peptides having an amino acid sequence that comprises about 11 to 13 contiguous amino acids of accession number: NP_034418. Other connexin inhibitors include a peptide having an amino acid sequence that comprises at least about 5, at least about 6, at least about 7, at least about 8, at least, about 9, at least about 10, at least about 11, at least about 12, at least about 13, at least about 14, at least about 15, at least about 20, at least about 25, or at least about 30 contiguous amino acids of accession number: NP_034418. Other connexin inhibitors comprise the extracellular domains of connexin 43 corresponding to the amino acids at positions 37-76 and 178-208 of accession number: NP_034418. Connexin inhibitors include peptides described herein that have an amino acid sequence corresponding to the regions at positions 37-76 and 178-208 of accession number: NP_034418. The peptides need not have an amino acid sequence identical to those portions of accession number: NP_034418, and conservative amino acid changes may be made such that the peptides retain binding activity or functional activity. Alternatively, peptides may target regions of the connexin protein other than, the extracellular domains (e.g., the portions of accession number: NP_034418 not corresponding to positions 37-76 and 178-208).

The anti-connexin peptides may comprise sequences corresponding to a portion of the connexin extracellular domains with conservative amino acid substitutions such that peptides are functionally active connexin inhibitors. Exemplary conservative amino acid substitutions include, for example, the substitution of a nonpolar amino acid with another nonpolar amino acid, the substitution of an aromatic amino acid with another aromatic amino acid, the substitution of an aliphatic amino acid with another aliphatic amino acid, the substitution of a polar amino acid with another polar amino acid, the substitution of an acidic amino acid with another acidic amino acid, the substitution of a basic amino acid with another basic amino acid, and the substitution of an ionizable amino acid with another ionizable amino acid.

Examples of peptides targeted to connexin 43 are shown below as SEQ ID NOs: 15 to 23:

```
FEVAFLLIQWI            (SEQ ID NO: 15)
LLIQWYIGFSL            (SEQ ID NO: 16)
SLSAVYTCKRDPCPHQ       (SEQ ID NO: 17)
VDCFLSRPTEKT           (SEQ ID NO: 18)
SRPTEKTIFII            (SEQ ID NO: 19)
LGTAVESAWGDEQ          (SEQ ID NO: 20)
QSAFRCNTQQPG           (SEQ ID NO: 21)
QQPGCENVCYDK           (SEQ ID NO: 22)
VCYDKSFPISHVR          (SEQ ID NO: 23)
```

Examples of peptides targeted to Cx32, Cx40, or Cx43 are shown below as SEQ ID NOs: 24 to 37:

Peptides targeted to Cx32 (SEQ ID NO: 34 is targeted to Cx32/Cx43)

```
ESVWGDEKSSFI                 (SEQ ID NO: 24)
ICNTLQPGCNSV                 (SEQ ID NO: 25)
SVCYDHFFPISH                 (SEQ ID NO: 26)
RLVKCEAFPCPNTVDCFVSRPTEKT    (SEQ ID NO: 27)
VKCEAFPCPNTV                 (SEQ ID NO: 28)
VDCFVSRPTEKT                 (SEQ ID NO: 29)
VCYDHFFPISHVR                (SEQ ID NO: 30)
VWGDEKSSFICNTLQPGY           (SEQ ID NO: 31)
DEKSSFICNTLQPGY              (SEQ ID NO: 32)
SRPTEKTVFTV                  (SEQ ID NO: 33)
SRPTEKT                      (SEQ ID NO: 34)
ICNTLQPGCNSV                 (SEQ ID NO: 35)

Peptide targeted to Cx40
FLDTLHVCRRSPCPHP             (SEQ ID NO: 36)

Peptide targeted to Cx43
KRDPCHQVDCFLSRPTEK           (SEQ ID NO: 37)
```

SEQ ID NOs: 38 to 65 indicate inhibitors of human connexins (huCx) 26, 30, 30.3, 31.1, 32, 36, 37, 40, 40.1, 43, 45, 46, and 46.6 for use as described herein.

```
                                                 (SEQ ID NO: 38)
huCx26     KEVWGDEQADFVCNTLQPGCKNVCYDHYFPISHIR (SEQ ID NO: 39)
huCx30     QEVWGDEQEDFVCNTLQPGCKNVCYDHFFPVSHIR (SEQ ID NO: 40)
huCx30.3   EEVWDDEQKDFVCNTKQPGCPNVCYDEFFPVSHVR (SEQ ID NO: 41)
huCx31     ERVWGDEQKDFDCNTKQPGCTNVCYDNYFPISNIR (SEQ ID NO: 42)
huCx31.1   ERVWSDDHKDFDCNTRQPGCSNVCFDEFFPVSHVR
```

```
huCx32      ESVWGDEKSSFICNTLQPGCNSVCYDQFFPISHVR     (SEQ ID NO: 43)

huCx36      ESVWGDEQSDFECNTAQPGCTNVCYDQAFPISHIR     (SEQ ID NO: 44)

huCx37      ESVWGDEQSDFECNTAQPGCTNVCYDQAFPISHIR     (SEQ ID NO: 45)

huCx40.1    RPVYQDEQERFVCNTLQPGCANVCYDVFS PVSHLR    (SEQ ID NO: 46)

huCx43      ESAWGDEQSAFRCNTQQPGCENVCYDKSFPISHVR     (SEQ ID NO: 47)

huCx46      EDVWGDEQSDFTCNTQQPGCBNVCYBRAFPISHIR     (SEQ ID NO: 48)

huCx46.6    EAIYSDEQAKFTCNTRQPGCDNVCYDAFAPLSHVR     (SEQ ID NO: 49)

huCx40      ESSWGDEQADFRCDTIQPGCQNVCTDQAFPISHIR     (SEQ ID NO: 50)

huCx45      GESIYYDEQSKFVCNTEQPGCENVCYDAFAPLSHVR    (SEQ ID NO: 51)

huCx26      MYVFYVMYDGFSMQRLVKCNAWPCPNTVDCFVSRPTEKT (SEQ ID NO: 52)

huCx30      MYVFYFLYNGYHLPWVLKCGIDPCPNLVDCFISRPTEKT (SEQ ID NO: 53)

huCx30.3    LYIFHRLYKDYDMPRVVACSVEPCPHTVDCYISRPTEKK (SEQ ID NO: 54)

huCx31      LYLLHTLWHGFNMPRLVQCANVAPCPNIVDCYIARPTE  (SEQ ID NO: 55)

huCx31.1    LYVFHSFYPKYILPPVVKCHADPCPNIVDCFISKPSEKN (SEQ ID NO: 56)

huCx32      MYVFYLLYPGYAMVRLVKCDVYPCPNTVDCFVSRPTEKT (SEQ ID NO: 57)

huCx36      LYGWTMEPVFVCQRAPCPYLVDCFVSRPTEKT        (SEQ ID NO: 58)

huCx37      LYGWTMEPVFVCQRAPCPYLVDCFVSRPTEKT        (SEQ ID NO: 59)

huCx40.1    GALHYFLFGFLAPKKFPCTRPPCTGVVDCYVSRPTSKS  (SEQ ID NO: 60)

huCx43      LLIQWYIYGFSLSAVYTCKRDPCPHQVDCFLSRPTEKT  (SEQ ID NO: 61)

huCx46      IAGQYFL YGFELKPLYRCDRWPCPNTVDCFISRPTEKT (SEQ ID. NO: 62)

huCx46.6    LVGQYLLYGFEVRPFFPCSRQPCPHVVDCFVSRPTEKT  (SEQ ID NO: 63)

huCx40      IVGQYFIYGIFLTTLHVCRRSPCPHPVNCYSRPTEKN   (SEQ ID NO: 64)

huCx45      LIGQYFLYGFQVHPFYVCSRLPCHPKIDCFISRPTEKT  (SEQ ID NO: 65)
```

SEQ ID NOs: 18 to 19 and 66 to 79 provide the extracellular domains of connexin family members (human connexins (huCx) 26, 30, 30.3, 31.1, 32, 36, 37, 40, 40.1, 43, 45, 46, and 46.6) that constitute connexin inhibitors (peptides). Such connexin inhibitors may comprise from about 8 to about 15, or from about 11 to about 13 contiguous amino acids of the peptides in SEQ ID NOs: 18 to 19 and 66 to 79. Conservative amino acid changes may be made to the peptides or fragments thereof.

```
huCx43      LLIQWYIYGFSLSAVYTCKRDPCPHQVDCFLSRPTEKTIFII    (SEQ ID NO: 66)

huCx26      MYVFYVMYDGFSMQRLVKCNAWPCPNTVDCFVSRPTEKTVFTV   (SEQ ID NO: 67)

huCx30      YVFYFLYNGYHLPWVLKCGIDPCPNLVDCFISRPTEKTVFTI    (SEQ ID NO: 68)

huCx30.3    LYIFHRLYKDYDMPRVVACSVEPCPMTVDCYISRPTEKKVFTY   (SEQ ID NO: 69)

huCx31      LYLLHTLWHGFNMPRLVQCANVAPCPNIVDCYIARPTEKKTY    (SEQ ID NO: 70)

huCx31.1    LYVFHSFYPKYILPPVVKCHADPCPNrVDCFISKPSEKNIFTL   (SEQ ID NO: 71)

huCx32      MYVFILLYPGYAMVRLVKCDVYPCPNTVDCFVSRPTEKTVFTV   (SEQ ID NO: 72)

huCx36      LYGWTMEPVFVCQRAPCPYLVDCFVSRPTEKTIFII          (SEQ ID NO: 73)

huCx37      LYGWTMEPVFVCQRAPCPYLVDCFVSRPTEKTIFII          (SEQ ID NO: 74)

huCx40.1    GALHYFLFGFLAPKKFPCTRPPCTGVVDCYVSRPTEKSLLML    (SEQ ID NO 75)

huCx46      IAGQYFLYGFELKPLYRCDRWPCPNTVDCFISRPTEKTIFII    (SEQ ID NO: 76)

huCx46.6    LVGWYLLYGFEVRPFFPCSRQPCPHVVDCFVSRPTEKTVFLL    (SEQ ID NO: 77)

huCx40      IVGQYFIYGIFLTTLHVCRRSPCPHPVNCYSRPTEKNVFIV     (SEQ ID NO: 78)

huCx45      LIGQYFLYGFQVHPFYVCSRLPCHPKIDCFISRPTEKTIFLLC   (SEQ ID NO: 79)
```

SEQ ID NOs: 80 to 92 and partial peptides thereof shown below provide peptides inhibitors of connexin 40 shown with reference to the extracellular loops (E1 and E2) of connexin 40.

```
E1
LGTAAESSWGDEQADFRCDTIQPGCQNVCTDQAYPISHIRFWVLQ   (SEQ ID NO: 80)

LGTAAESSWGDEQA                                  (SEQ ID NO: 81)

DEQADERCDTIQP                           (SEQ ID NO: 82)

TIQPGCQNVCTDQ                       (SEQ ID NO: 83)
```

```
                            (SEQ ID NO: 84)
                 VCTDQAFPISHIR (SEQ ID NO: 85)
                 AFPISHIRFWVLQ

E2
                            (SEQ ID NO: 86)
MEVGFIVGQYFIYGIFLTTLHVCRRSPCPHPVNCYVSRPTEKNVFIV (SEQ ID NO: 87)
MEVGFIVGQYF (SEQ ID NO: 88)
       IVGQYFIYGIFL (SEQ ID NO: 89)
            GIFLTTLHVCRRSP (SEQ ID NO: 90)
                 RRSPCPHPVNCY (SEQ ID NO: 91)
                    VNCYVSRPTEKN (SEQ ID NO: 92)
                       SRPTEKNVFIV
```

SEQ ID NOs: 93 to 105 provide peptides inhibitors of connexin 45 shown with reference to the extracellular loops (E1 and E2) of connexin 45.

```
E1
                            (SEQ ID NO: 93)
LTAVGGESIYYDEQSKFVCNTEQPGCENVCYDAFAPLSHVRFWVFQ (SEQ ID NO: 94)
LTAVGGESIYYDEQS (SEQ ID NO: 95)
     DEQSKFVCNTEQP (SEQ ID NO: 96)
          TEQPGCENVCYDA (SEQ ID NO: 97)
               VCYDAFAPLSHVR (SEQ ID NO: 98)
                    APLSHVRFWVFQ

E2
                            (SEQ ID NO: 99)
FEVGFLIGQFLYGFQVHPFYVCSRLPCHPKIDCFISRPTEKTIFLL (SEQ ID NO: 100)
FEVGFLIGQYF (SEQ ID NO: 101)
     LIGQYFLYGFQV (SEQ ID NO: 102)
         GFQVHPFYVCSRLP (SEQ ID NO: 103)
              SRLPCMPKIDCF (SEQ ID NO: 104)
                  IDCFISRPTEKT (SEQ ID NO: 105)
                     SRPTEKTIFLL
```

Examples of inhibitors (peptides) of connexin 45 are as follows:

| Sequence | ID |
|---|---|
| YVCSRLPCHP | (SEQ ID NO: 106) |
| QVHPFYVCSRL | (SEQ ID NO: 107) |
| FEVGFLIGQYFLY | (SEQ ID NO: 108) |
| GQYFLYGFQVHP | (SEQ ID NO: 109) |
| GFWVHPFYVCSR | (SEQ ID NO: 110) |
| AVGGESIYYDEQ | (SEQ ID NO: 111) |
| YDEQSKFVCNTE | (SEQ ID NO: 112) |
| NTEWPGCENVCY | (SEQ ID NO: 113) |
| CYDAFAPLSHVR | (SEQ ID NO: 114) |
| FAPLSHVRFWVF | (SEQ ID NO: 115) |
| LIGQY | (SEQ ID NO: 116) |
| QVHPF | (SEQ ID NO: 117) |
| YVCSR | (SEQ ID NO: 118) |
| SRLPC | (SEQ ID NO: 119) |
| LPCHP | (SEQ ID NO: 120) |
| GESIY | (SEQ ID NO: 121) |
| YDEQSK | (SEQ ID NO: 122) |
| SKFVCN | (SEQ ID NO: 123) |
| TEQPGCEN | (SEQ ID NO: 124) |
| VCYDAFAP | (SEQ ID NO: 125) |
| LSHVRFWVFQ | (SEQ ID NO: 126) |

The antibodies and peptides used, as connexin inhibitors may be commercial products. Examples of Cx43 antibodies include Cat, No: Sigma, C-6219; Zymed, 13-8300; Santa Cruz, sc-6560; etc. Examples of Cx43-inhibiting peptides include Cat. No: Santa Cruz, sc-6560 P; BD Transduction Laboratories, 610063; and Abeam, ab56616.

TGFβ signaling inhibitors are defined as agents that inhibit TGF-β signal transduction, including TGF-β antagonists known in the art. For example, agents that bind to TGF-β receptor I and prevent TGF-β from binding to the TGF-β receptor act as TGF-β signaling inhibitors.

Other non-limiting examples include blocking (neutralizing) antibodies specific for a human TGF-β (NAb), such as those described by Dasch et al. (J. Immunol. (1989) 142: 1536) and Lucas et al. (J. Immunol. (1990) 145: 1415), soluble TGF-β receptors, membrane-bound TGF-β receptors, protease inhibitors that inactivate a protease responsible for activating a precursor TGF-β into mature TGF-β, antibodies that are specific to TGF-β receptors (Type I, II, or III) and prevent TGF-β binding to the receptor, and combinations thereof.

Figure 4:
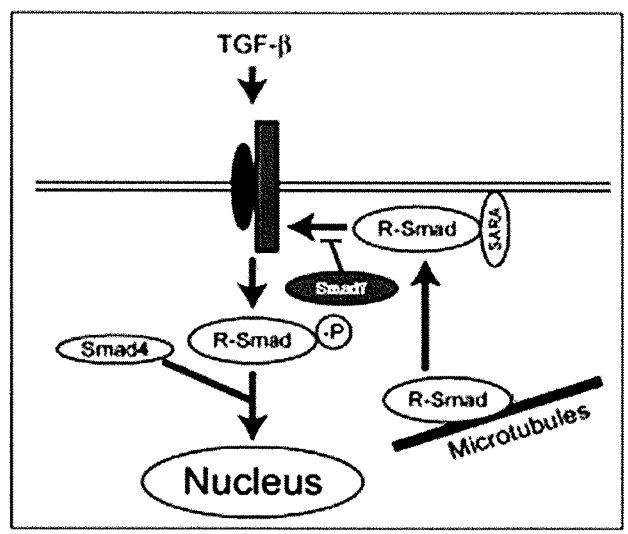
FIG. 4 schematically illustrates TGF-β signaling.

The TGF-β signal transduction is described with reference to FIG. 4.

Ligand TGF-β binds to TGF-β receptor II (TβRII) to thereby activate TβRII. The activated TβRII is polymerized with TGF-β receptor I (TβRI) to form a tetramer composed of two TβRI and two TβRII, and phosphorylation occurs in the C terminus of TβRI. The phosphorylated TβRI becomes an active form. To the C terminus of the phosphorylated TβRI, Smad2 and Smad3 (mediators of TGF-β signaling) are supplied and phosphorylated. The phosphorylated Smad2 and Smad3 bind to Smad4 localized in the cytoplasm, and nuclear translocation occurs, followed by binding to the target gene, thereby affecting the expression of the target gene.

The TGF-β signaling inhibitors of the present invention inhibit any one of the above signal transduction pathways. Accordingly, substances having functions, such as inhibition of TGF-β expression, inhibition of TβRI or TβRII expression, inhibition of the binding of TGF-β to TβRII, inhibition of the formation of a tetramer composed two TβRI and two TβRII, inhibition of the phosphorylation of the C terminus of TβRI, dephosphorylation of the C terminus of TβRI, ubiquitination of TβRI, inhibition of the phosphorylation of Smad2 and Smad3, inhibition of the expression of Smad2 and Smad3, ubiquitination of Smad2 and Smad3, dephosphorylation of phosphorylated Smad2 and Smad3, and inhibition of the binding of phosphorylated Smad2 and Smad3 to Smad4, can function as TGF-β signaling inhibitors in the present invention.

The TGF-β signaling inhibitors may be commercial products. Such commercial products are divided into (1) those inhibiting receptors, and (2) those inhibiting downstream signal transduction of the receptors.
(1) Receptor I (ALK 5) inhibitor:
SR425342, A-83-01, and ALK5 inhibitors
(2) Signal transduction inhibitor:
Inhibitor Smad: Smad7 binds to TβRI so as to inhibit the binding of Smad2 and Smad3 to TβRI.
Signaling mediator inhibition: siRNA or antisense oligo DNA inhibits the expression of Smad2, Smad3, and Smad4.

The TGF-β signaling inhibitors widely include commercially available Receptor I (ALK 5) inhibitors (e.g., SB425342, A-83-01, and ALK5 inhibitors) and substances that mimic the function of signal transduction inhibitors.

The TGF-β signaling inhibitors include antibodies against TGFβ, TβRI, and TβRII. The antibodies include, as described regarding connexin inhibitors, monoclonal antibodies, polyclonal antibodies, antibody fragments (including, for example, Fab, F(ab')$_2$, and Fv fragments); single-chain antibodies; single-chain Fvs; and single-chain binding molecules (e.g., those comprising, for example, a binding domain, hinge, CH2 and CH3 domains), recombinant antibodies and antibody fragments that, are capable of binding an antigenic determinant (i.e., that portion of a molecule, generally referred to as an epitope) that makes contact with a particular antibody or other binding molecule.

The TGF-β signaling inhibitors include substances that prevent the conversion of TGF-β precursor into mature TGF-β, and also include soluble TGF-β receptors.

TGF-β is generally secreted as a latent precursor consisting of TGF-β non-covalently associated, with a protein, designated latency-associated protein (LAP; Harpel et al. (1992) Prog. Growth Factor Res. 4: 321). This latent complex requires enzymatic cleavage of carbohydrate groups or transient acidification to release the active cytokine. Purified LAP by itself binds active TGF-β with high affinity to form a latent complex. A DNA encoding a 278 amino acid peptide corresponding to pre-pro-TGF-β, terminating just prior to the mature form of TGF-β and containing a Cys33 to Ser33 substitution has been expressed (Derynck et al. (1985) Nature 316: 701), and found to bind TGF-β and render it latent.

Soluble forms of TGF-β receptors will also bind TGF-β and prevent binding to membrane-associated TGF-β receptors. TGF-β receptors are described by Wang et al. (Cell (1991) 67: 797) and Lin et al. (Cell (1992) 68: 775). Soluble forms of TGF-β receptors may be prepared by methods that are known in the art. For example, deletion mutants lacking the transmembrane domain of a TGF-β receptor can be prepared, which will express a soluble TGF-β binding protein (Miyazono et al. (Adv. Immunol. (1994) 55: 181).

Other types of TGF-β antagonists that function as TGF-β signaling inhibitors are also known in the art. For example, Yamaguchi et al. (Nature (1990) 346: 281) discuss decorin, a small chondroitin-dermatan sulphate proteoglycan that binds TGF-β and modulates the activity of this growth factor. Ohtsuki and Massague (Mol. Cell. Biol. 12: 261-265, 1992) disclose protein kinase inhibitors that block certain biological activities of TGF-β. The design and use of protease inhibitors as drugs is well known in the art (Design of Enzyme Inhibitors as Drugs; Sandler and Smith, eds; 1989, Oxford University Press; Proteinase Inhibitors Medical and Biological Aspects; Katunuma, Umezawa and Holzer, eds., 1983, Springer-Verlag); thus, inhibitors of cruzain van be prepared, and will be useful as TGF-β antagonists.

Still other TGF-β antagonists and methods for their production are well known in the art, with many more currently under development. The specific TGF-β antagonist employed, is not a limiting feature, as any effective TGF-β antagonist may be useful in this invention. Examples of such antagonists include monoclonal and polyclonal antibodies directed against one or more isoforms of TGF-β (U.S. Pat. No. 5,571,714 and WO 97/13844), TGF-β receptors, fragments thereof, derivatives thereof and antibodies directed against TGF-β receptors (U.S. Pat. Nos. 5,693,607, 6,008, 011, 6,001,969 and 6,010,872; and WO 92/00330, WO 93/09228, WO 95/10610 and WO 98/48024); latency-associated peptide (WO 91/08291), large latent TGF-β (WO 94/09812), fetuin (U.S. Pat. No. 5,821,227), decorin and other proteoglycans, such as biglycan, fibromodulin, lumican and endoglin (U.S. Pat. Nos. 5,583,103, 5,654,270, 5,705, 609, 5,726,149, 5,824,655, 5,830,847, and 6,015,693; and WO 91/04748, WO 91/10727, WO 93/09800 and WO 94/10187).

Further examples of such antagonists include somatostatin (WO 98/08529), mannose-6-phosphate or mannose-1-phosphate (U.S. Pat. No. 5,520,926), prolactin (WO 97/40848), insulin-like growth factor II (WO 98/17304), IP-10 (WO 97/00691), arg-gly-asp-containing peptides (U.S. Pat. No. 5,958,411 and WO 93/10808), extracts of plants, fungi and bacteria (European Patent Application No. 813875, Japanese Patent Application No. 81-19984 and U.S. Pat. No. 5,693, 610), antisense oligonucleotides (U.S. Pat. Nos. 5,683,988, 5,772,995, 5,821,234 and 5,869,462; and WO 94/25588), and other proteins involved in TGF-β signaling, including SMADs and MADs (European Patent Application EP 874046; WO 97/31020, WO 97/38729, WO 98/03663, WO 98/07735, WO 98/07849, WO 98/45467, WO 98/53068, WO 98/55512, WO 98/56913, WO 98/53830 and WO 99/50296; and U.S. Pat. Nos. 5,834,248, 5,807,708 and 5,948,639) and Ski and Sno (G. Vogel, Science, 286: 665 (1999) and Stroschein et al., Science, 286: 771-74 (1999)) and fragments and derivatives of any of the above molecules that retain the ability to inhibit the activity of TGF-β.

TGF-β receptors and TGF-β-binding fragments of TGF-β receptors, especially soluble fragments, are useful TGF-β antagonists in the methods of the present invention. TGF-β receptors and the nucleic acids encoding them are well known in the art. The nucleic acid sequence encoding TGF-β type 1 receptor is disclosed in GenBank accession number L15436 and in U.S. Pat. No. 5,538,892 of Donahoe et al. The nucleic acid sequence of TGF-β type 2 receptor is publicly available under GenBank accession numbers AW236001; AI35790; AI279872; AI074706; and AA808255. The nucleic acid sequence of TGF-β type 3 receptor is also publicly available under GenBank accession numbers NM003243; AI887852; AI817295; and AI681599. In a preferred, embodiment, the TGF-β antagonist is an antibody that blocks TGF-β binding to its receptor, or: fragments thereof, such as $F(ab)_2$ fragments, Fv fragments, single-chain antibodies and other forms of "antibodies" that retain the ability to bind to TGF-β. The antibody may be chimerized or humanized.

Other examples include an RNA sequence that acts as RNAi against TGFβ1 receptor II (Japanese Patent Publication No. 2005-253344), siRNA for silencing of TGFβII receptor expression (Japanese Patent Publication No. 2007-502284), pyrimidinylimidazole as a TGF-β inhibitor (Japanese Patent Publication No. 2008-511631), pyrimidinylpyrazole (Japanese Patent Publication No. 2008-511630), and the like.

Preferred TGF-β signaling inhibitors are SB-431542, A-83-01, and ALK5 inhibitors.

The TGF-β signaling inhibitors can be added to the medium of the cells. The concentration is, for example, an effective amount of the TGF-β signaling inhibitor used. In the case of SB-431542, for example, the concentration is about 1 to 100 μM, and preferably about 10 μM.

The connexin inhibitor can be incorporated into the cells by adding the connexin inhibitor in an amount not less than the effective amount to the medium. For example, in the case of siRNA, about 10 to 1,000 nM, and preferably about 100 nM of the connexin inhibitor can be added to the medium. The amounts of TGF-β signaling inhibitors and connexin inhibitors other than those mentioned above can be easily determined by those skilled in the art.

Examples of the cells to be used as the starting material of the iPS cells include all types of somatic cells, such as cardiomyocytes, fibrocytes, skin cells, muscle cells, and fat cells. Such somatic cells are preferably those that express connexins, and more preferably those that highly express connexins.

The iPS cells can be obtained from mammalian cells (e.g., human, mouse, rat, cattle, horse, pig, rabbit, sheep, goat, monkey, dog, and cat) or animal cells (e.g., chicken, duck, and xenopus).

The connexin inhibitor and TGFβ signaling inhibitor may be reacted with the cells simultaneously or sequentially. Preferably, these inhibitors are simultaneously reacted with the cells.

From the iPS cells obtained by reacting the cells with the connexin inhibitor and TGF-β signaling inhibitor, a group of iPS cells can be separated and purified by removing non-iPS cells according to a general method.

At the time when the iPS cells of the present invention are induced by reacting the cells with the connexin inhibitor and TGF-β signaling inhibitor, either one or both of the connexin inhibitor and TGF-β signaling inhibitor is presumably present in the cells. In particular, when these inhibitors are molecules that inhibit gene expression in the cells, they are considered to be present in the cells at the moment when the cells turn into iPS cells. In particular, the connexin inhibitor is not conventionally used in the production and culture of iPS, and the iPS cells comprising the connexin inhibitor are novel.

The connexin inhibitor and TGF-β signaling inhibitor both can be used to induce iPS cells, and are thus useful as iPS cell inducers.

The medium comprising at least one inhibitor selected from the group consisting of connexin inhibitors and TGFβ signaling inhibitors can induce iPS cells, and is thus useful as a medium for inducing iPS cells.

Furthermore, at least one inhibitor selected from the group consisting of connexin inhibitors and TGF-β signaling inhibitors can induce iPS cells, and is thus useful as a kit for inducing iPS cells.

EXAMPLES

The present invention is described in detail below according to Examples.

Example 1

Reprogramming of Cardiomyocytes Derived from Neonatal Mouse Ventricles

Target and Method
1) Isolation of Cardiomyocytes

Two-day-old neonatal C57BL/6 or C57BL/6-Tg (CAG-EGFP) mouse hearts including ventricles were minced into approximately 2-mm cubes with dissecting scissors by a conventional method. They were treated with 0.2% collagenase (type II; Worthington Biochemical Corp. U.S.; dissolved in PBS) to dissociate cardiomyocytes. The dissociated cardiomyocytes were centrifuged, and incubated for 45 minutes in DMEM containing 10% FBS at 37° C. with 5% $CO_2$. After the incubation, the supernatant was further incubated under the same conditions. This process was repeated four times. Thus, fibroblasts were removed, and the cardiomyocytes were isolated,
2) Reprogramming from Cardiomyocytes:

The cardiomyocytes were seeded at $2\times10^5$ cells in a 6-cm dish, and cultured in the above DMEM medium. After culturing for 1 week, the medium used for culturing the cardiomyocytes was switched from the above DMEM medium to mouse ES media containing 15% FBS and also containing either a TGF-β receptor inhibitor SB-431542 (10 μM; Tocris, USA), siRNA Cx43 (100 nM), or both compounds, to select the reprogrammed cells.

The mouse Cx43 siRNA sequences used are as follows:

```
sense:       5'-CAA UUC CUC CUG CCG CAA TT-3' antisense:   5'-UUG CGG CAG GAG GAA UUG TT-3'
```

3) Evaluation of Pluripotency
(i) Cell Immunostaining of Early Marker of Es Cells Two iPS cell colonies were obtained after about two weeks from cardiomyocytes that were selectively cultured in the ES medium containing both 10 μM SB-431542 and 100 nM siRNA Cx43, iPS-like cells grown by culturing on feeder cells under the same conditions as mouse ES cell culture conditions were used for immunostaining, etc., and for confirmation of teratoma formation.

Measurement of alkaline phosphatase (ALP) was performed using an Alkaline Phosphatase Detection Kit (Millipore, USA).

The antibodies used in cell immunostaining are as follows:
rabbit anti-Nanog antibody (diluted 200 times, Cosmo Bio.; REC-RAB004 PF),
rabbit anti-Oct4 antibody (diluted 500 times; sc-9081),
goat anti-Sox2 antibody (diluted 200 times; sc-17320), and
mouse anti-SSEA1 antibody (diluted 200 times; sc-21702).
(ii) Teratoma Formation The iPS-like cells ($2\times10^5$) were implanted subcutaneously in SCID mice. After five weeks, tumors were removed, and whether teratomas would be formed was histologically confirmed by HE staining.

(iii) Production of Chimeric Mice

The iPS-like cells were implanted in eight-celled fertilized eggs derived from ICR mice, and the eggs were returned to the ICR mice. Then, it was confirmed whether chimeric mice would be produced.

Results

1. Expression of ES Early Marker Gene

Figure 2:
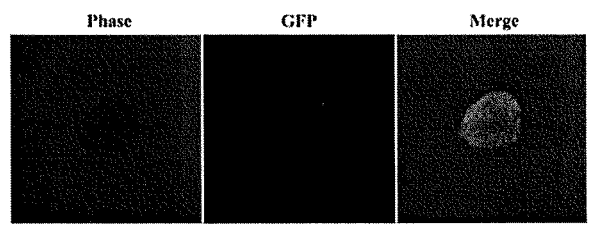
FIG. 2 snows the morphology of siPSCs derived from EGFP mouse myocardium.

The two iPS cells derived from mouse cardiomyocytes produced in the present invention, siPSCs (silencing-induced pluripotent stem cells), were morphologically similar to a mouse ES cell colony (FIG. 1a); ALP activity was confirmed (FIG. 1b); and the expression of the pluripotency marker factors, Nanog, Oct4, Sox2, and SSEA1, was confirmed at the protein level (FIG. 1c). Moreover, the expression of various pluripotency marker genes was also confirmed at the gene level (FIG. 1a). Furthermore, the induction of the iPS-like cells from the EGFP mouse cardiomyocytes was also confirmed (FIG. 2).

2. Verification of Differentiation Potency of siPSCs iPSCs were implanted subcutaneously in SCID mice. After five weeks, teratomas consisting of all three embryonic germ layers, such as epidermal and neural tissues (ectoderm), muscles and cartilage (mesoderm), and gland (endoderm), were formed (FIG. 1e). Although no data is provided, it was confirmed that siPSCs formed blastoderms, which were able to differentiate into neurons, cardiomyocytes, or endothelial cells, depending on differentiation-inducing conditions. Beat and conduction were observed in the cardiomyocytes. Further, in the cells differentiation-induced by immunostaining and RT-PCR, the expression of three embryonic germ layer marker gene was confirmed at both protein and gene levels.

3. Production of Chimeric Mice

Figure 3:
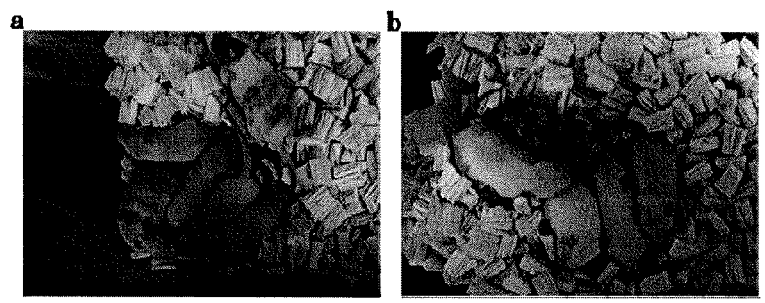
FIG. 3 shows the production of chimeric mice from siPSCs cells.
  a. Chimeric mice generated, from siPSCs-#1.
  b. Chimeric mice generated from siPSCs-#2.

The two iPS cells derived from mouse cardiomyocytes produced in the present invention were injected into blastocysts to thereby generate adult chimeric mice containing a mixture of cells derived from the iPS cells. This result, suggests that the iPS cells have differentiation pluripotency equivalent to that of ES cells (FIG. 3).

The patent documents and papers referred to herein are incorporated herein by reference in their entireties.

INDUSTRIAL APPLICABILITY

The method of the present invention can produce iPS cells safely and readily; therefore, the present invention provides a highly effective means for clinical application of iPS cells in the future.

The invention claimed is:

1. A method for producing induced pluripotent stem (iPS) cells, comprising culturing isolated mammalian somatic cells in ES medium comprising a connexin inhibitor and a TGFβ signaling inhibitor to produce iPS cells expressing ES cell markers.

2. The method according to claim 1, wherein the connexin inhibitor is a connexin 43 inhibitor.

3. The method according to claim 1, wherein the connexin inhibitor is an siRNA, an shRNA, an miRNA, or an antisense RNA specific for connexin, a peptide, an antibody specific for connexin, or ribozyme against connexin, or a vector that expresses a connexin RNA molecule inhibitor when introduced into the somatic cells.

4. The method according to claim 1, wherein the TGFβ signaling inhibitor is a TGF-β receptor I inhibitor.

5. The method according to claim 1, wherein the TGF-β receptor inhibitor is SB-431542, A-83-01, or ALK5 inhibitor.

6. A mammalian iPS cell comprising a connexin inhibitor and a TGFβ signaling inhibitor.

7. The iPS cell according to claim 6, wherein the connexin inhibitor is a connexin 43 inhibitor.

8. The iPS cell according to claim 6, wherein the connexin inhibitor is an siRNA, an shRNA, an miRNA, or an antisense RNA specific for connexin, a peptide, and antibody specific for connexin, or ribozyme against connexin, or a vector that expresses a connexin RNA molecule inhibitor when introduced into the somatic cells.

9. An iPS cell inducer comprising a connexin inhibitor and a TGFβ signaling inhibitor.

10. A medium for inducing iPS cells, comprising a connexin inhibitor and a TGF-β signaling inhibitor.

11. A kit for inducing iPS cells, comprising a connexin inhibitor and a TGF-β signaling inhibitor.

* * * * *